(12) United States Patent
Choi et al.

(10) Patent No.: US 9,370,542 B2
(45) Date of Patent: Jun. 21, 2016

(54) **MEDICAL COMPOSITION CONTAINING *STAUNTONIA HEXAPHYLLA* EXTRACT**

(75) Inventors: Chul Yung Choi, Gwangju (KR); Sang O Pan, Gwangju (KR); Hee Jin Seol, Gwangju (KR); Gyu Ok Lee, Jangheung-gun (KR); Ka Hyon Park, Jangheung-gun (KR); Hee Sook Kim, Goseong-gun (KR); Wook Jin Jang, Jangheung-gun (KR); Hyun Kim, Gwangju (KR); Dong Wook Lee, Jangheung-gun (KR); Sun Oh Kim, Gwangju (KR); Jae Gap Kim, Bucheon-si (KR)

(73) Assignees: JEONNAM BIOINDUSTRY FOUNDATION, Naju-Si (KR); YUNGJIN PHARM.CO., LTD., Seoul (KR)

( * ) Notice: Subject to any disclaimer, the term of this patent is extended or adjusted under 35 U.S.C. 154(b) by 0 days.

(21) Appl. No.: 14/239,521

(22) PCT Filed: May 16, 2012

(86) PCT No.: PCT/KR2012/003867
§ 371 (c)(1),
(2), (4) Date: Mar. 19, 2014

(87) PCT Pub. No.: WO2013/024960
PCT Pub. Date: Feb. 21, 2013

(65) Prior Publication Data
US 2014/0205691 A1    Jul. 24, 2014

(30) Foreign Application Priority Data

Aug. 18, 2011  (KR) .......................... 10-2011-0082023
Apr. 16, 2012  (KR) .......................... 10-2012-0038977
May 11, 2012  (KR) .......................... 10-2012-0050532

(51) Int. Cl.
*A61K 36/185*    (2006.01)

(52) U.S. Cl.
CPC .................................... *A61K 36/185* (2013.01)

(58) Field of Classification Search
None
See application file for complete search history.

(56) References Cited

FOREIGN PATENT DOCUMENTS

| CN | 1562275 A | 1/2005 |
|---|---|---|
| CN | 1742816 A | 3/2006 |
| CN | 1823993 A | 8/2006 |
| CN | 101024065 A | 8/2007 |
| CN | 101283784 A | 10/2008 |
| CN | 101926488 A | 12/2010 |
| CN | 102132914 A | 7/2011 |
| JP | 1-242596 A | 9/1989 |
| JP | 2001-226249 A | 8/2001 |
| KR | 10-2009-0048848 A | 5/2009 |
| KR | 10-2011-0068923 A | 6/2011 |

OTHER PUBLICATIONS

Kim (Food Chemistry (2010), vol. 122, pp. 546-552).*
http://www.mayoclinic.org/diseases-conditions/multiple-sclerosis/expert-answers/vitamin-d-and-ms/faq-20058258—access Mar. 2015.*
Wang (Phytochemistry (1998), vol. 47, No. 3, pp. 467-470).*
Wang (Phytochemistry (1993), vol. 33, No. 6, pp. 1469-1473).*
G. Mahno, M.D., "Studies on Inflammation II. The Site of Action of Histamine and Serotonin along the Vascular Tree: A Topographic Study," The Journal of Biophysical and Biochemical Cytology, vol. 11, pp. 607-626, 1961.
KSBB Abstracts of 2011, Annals of of Bioengineering, vol. 28, Korean Society of Biotechnology and Bioengineering, p. 205, 2011.
Kim et al., "Antioxidant activity and cell toxicity of pressurised liquid extracts from 20 selected plant species in Jeju, Korea," Food Chemistry, 2010, vol. 122, pp. 546-552.
Ikuta, "Triterpenes from Stauntonia Hexaphylla Callus Tissues", Journal of Natural Products, vol. 55, No. 9, Sep. 1992, pp. 1230-1233.
Recio et al., "Structural Requirements for the Anti-Inflammatory Activity of Natural Triterpenoids", Planta Med. vol. 61, No. 2, Apr. 1995, pp. 182-185.
Tang et al. "Research on analgesic activity of a traditional Chinese drug stauntoniae," Journal of Pharmacological Sciences, 83rd Annual Meeting of the Japanese Pharmacological Society, vol. 112, No. Suppl. 1, p. 168P, 2010.
Chinese Office Action mailed Nov. 9, 2015 for application No. 2012800454043.0.
Science and Technology of Food Industry, vol. 27, No. 11, 2006 (3 pages) (with English Abstract).
Japanese Office Action and English Translation for JP Application No. 2014-525911 mailed Jan. 12, 2016.
Lee et al., Anti-inflammatory effects of Stauntonia hexaphylla in LPS-Induced Raw 264.7 macrophage, South Korean Society for Biotechnology, Japan spring scientific announcement convention, Apr. 2011, vol. 2011, No. 1, p. 205 (abstract).

* cited by examiner

*Primary Examiner* — Susan Hoffman
(74) *Attorney, Agent, or Firm* — Birch, Stewart, Kolasch & Birch, LLP

(57) ABSTRACT

Disclosed is an antipyretic drug comprising a *Stauntonia Hexaphylla* leaf extract as an active ingredient. The antipyretic drug is developed based on the finding that the *Stauntonia Hexaphylla* leaf extract has no cytotoxicity and exhibits superior antipyretic effects, as compared to conventional antipyretic drugs having antipyretic effects. An antipyretic composition comprising the *Stauntonia Hexaphylla* leaf extract as an active ingredient exhibits potent antipyretic effect.

5 Claims, 7 Drawing Sheets

```
                        SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: iNOS_Sense

<400> SEQUENCE: 1
cagaggaccc agagacaag                                                 19

<210> SEQ ID NO 2
<211> LENGTH: 20
<212> TYPE: DNA
<213> ORGANISM: Artificial Sequence
<220> FEATURE:
<223> OTHER INFORMATION: iNOS_Anti-sense

<400> SEQUENCE: 2
acctgatgtt gccattgttg                                                20

<210> SEQ ID NO 3
<211> LENGTH: 25
<212> TYPE: DNA
<213> ORGANISM: Artificial Sequence
<220> FEATURE:
<223> OTHER INFORMATION: TNF-a_Sense

<400> SEQUENCE: 3
ggcaggtcta ctttggagtc attgc                                          25

<210> SEQ ID NO 4
<211> LENGTH: 25
<212> TYPE: DNA
<213> ORGANISM: Artificial Sequence
<220> FEATURE:
<223> OTHER INFORMATION: TNF-a_Anti-sense

<400> SEQUENCE: 4
acattcgagg ctccagtgaa ttcgg                                          25

<210> SEQ ID NO 5
<211> LENGTH: 25
<212> TYPE: DNA
<213> ORGANISM: Artificial Sequence
<220> FEATURE:
<223> OTHER INFORMATION: IFN-r_Sense

<400> SEQUENCE: 5
gcggctgact gaactcagat tgtag                                          25

<210> SEQ ID NO 6
<211> LENGTH: 24
<212> TYPE: DNA
<213> ORGANISM: Artificial Sequence
<220> FEATURE:
<223> OTHER INFORMATION: IFN-r_Anti-sense

<400> SEQUENCE: 6
```

```
gtcacagttt tcagctgtat aggg                                               24

<210> SEQ ID NO 7
<211> LENGTH: 24
<212> TYPE: DNA
<213> ORGANISM: Artificial Sequence
<220> FEATURE:
<223> OTHER INFORMATION: IL-1b_Sense

<400> SEQUENCE: 7
tgcagagttc ctacatggtc aacc                                               24

<210> SEQ ID NO 8
<211> LENGTH: 25
<212> TYPE: DNA
<213> ORGANISM: Artificial Sequence
<220> FEATURE:
<223> OTHER INFORMATION: IL-1b_Anti-sense

<400> SEQUENCE: 8
gtgctgccta atgtcccctt gaatc                                              25
```

MEDICAL COMPOSITION CONTAINING *STAUNTONIA HEXAPHYLLA* EXTRACT

BACKGROUND OF THE INVENTION

1. Field of the Invention

The present invention relates to a composition comprising a *Stauntonia Hexaphylla* extract and use of the *Stauntonia Hexaphylla* extract.

2. Description of the Related Art

An inflammatory response is an immune response which locally occurs, when cells or tissues are damaged or broken due to various causes, for example, exposure to harmful substances or organic systems including external infectious agents such as bacteria, fungi, viruses or a variety of allergens, so that the damage is minimized and damaged sites are restored to an original state.

In addition, various causes inducing inflammation include physical causes such as trauma, burns, frostbite and radioactivity, chemical causes such as chemicals, for example acids, and immunological causes such as antibody response. Furthermore, inflammation may be caused by imbalance of vessels or hormones.

The inflammatory response is a defense mechanism which is useful for protecting biological systems and removing substances produced by tissue damage, and involves symptoms including enzymatic activation caused by inflammation-mediators and immunocytes present in local vessels or body fluids, secretion of inflammation-mediators, infiltration of body fluids, cell migration, tissue destruction, erythema, edema, fever, pain or the like. Such symptoms may cause dysfunction.

In a normal case, inflammation functions to remove external infectious agents or neutralize or remove disease factors and to regenerate damaged tissues and thereby to restore normal structures and functions through an in vivo inflammatory response. However, as antigens are not continuously removed or inflammation becomes serious over a predetermined level or chronic due to specific endogenous substances, diseases such as hypersensitiveness or chronic inflammation may disadvantageously propagate. Inflammatory response is found in most clinical diseases and enzymes involved in inflammatory response are known to play an important role in carcinogenesis. In addition, inflammation is an obstacle in the course of treatment such as blood transfusion, medication or organ transplantation.

An inflammatory response is involved in various biochemical events in vivo. In particular, inflammatory response is initiated or controlled by inflammatory response-associated enzymes produced by immunocytes.

As has recently been revealed, progression of in vivo inflammatory response is known to be involved in enzymatic activities of cyclooxygenase (COX). The COX enzyme is a main enzyme involved in biosynthesis of prostaglandin present in biological systems. Two iso-enzymes, i.e., COX-1 and COX-2, are known. COX-1 exists in tissues such as stomach or kidney and is responsible for maintenance of normal homeostasis. On the other hand, COX-2 is temporarily and rapidly expressed in cells by mitogens or cytokines upon inflammation or other immune responses.

Another potent inflammation mediator, nitric oxide (NO), is synthesized from L-arginine through NO synthetase (NOS) and is produced in various types of cells in response to exterior stress such as UV light, or substances such as endotoxins or cytokines. Such inflammation stimuli increase expression of inducible NOS (iNOS) in cells and induce production of NO in cells through iNOS, thus activating macrophage cells and resulting in inflammatory response.

Accordingly, research associated with substances inhibiting production of NO is recently underway for efficient alleviation of inflammation. However, anti-inflammatory substances developed through such research have several side effects. For example, nonsteroidal anti-inflammatory drugs used in the treatment of acute inflammatory diseases or chronic inflammatory diseases are known to inhibit both COX-2 enzymes and COX-1 enzymes and thus cause side effects such as gastrointestinal disorders.

Meanwhile, cosmetics are routinely used to protect the skin and realize beautification and cleanliness. However, cosmetic compositions utilize ingredients indispensable for formation of cosmetic products which are inconsistent with skin protection application. For example, the ingredients include surfactants, preservatives, flavorings, UV blockers, pigments and various ingredients to impart other efficacies and effects. The ingredients necessarily used for production of cosmetics are known to cause side effects, such as inflammation, pimples or edema, to the skin.

In addition, serum and sweat secreted from the body, and fatty acids, higher alcohols and proteins as cosmetic components are decomposed to highly toxic substances by resident flora present in the skin, thus inducing skin inflammation. It is well-known that UV light emitted from the sun may also induce skin inflammation.

As such, factors causing skin side effects are always potential in cosmetics and a variety of research has been made to solve the factors. Substances used to date to alleviate irritation such as erythema or edema and inflammation include non-steroid substances such as flufenamic acid, ibuprofen, benzydamine and indomethacin, steroid substances such as prednisolone and dexamethasone. Allantoin, azulene, ε-aminocaproic acid, hydrocortisone, licorice acid and derivatives thereof (β-glycyrrhizinic acid, glycyrrhizinic acid derivatives) are known to be effective in anti-inflammation.

However, indomethacin, generally used as an anti-inflammatory agent, is unsuitable for use in cosmetics, hydrocortisone has a limited dose, licorice acid and derivatives thereof do not provide substantial effects due to limited concentration upon practical application caused by difficulty in stabilization or poor solubility. Use of most anti-inflammatory agents known to date is limited due to problems in terms of skin safety or stability upon cosmetic mixing.

In addition, mechanisms of therapeutic agents associated with gastritis are primarily associated with H2-blockers which block the second histamine receptor (H2 receptor) to reduce secretion of gastric acid from parietal cells. The reduced gastric acid prevents additional damage of damaged parietal cells (such as gastric ulcers). Such H2-blockers disturb metabolisms of other drugs, that is, potent inhibitors of P-450 in the liver, and thus require attention when administered in combination with other drugs. H2-blockers may cause side effects such as gynecomastia, impotence and hypoactive sexual desire disorder may occur in men due to exhibit anti-androgen effects. In addition, H2-blockers pass through the placenta and cerebrovascular barriers, thus causing more dangerous side effects to pregnant women or the elderly, and resulting in headache, confusion, stupor or dizziness.

Accordingly, there is a need for substances which are derived from natural substances, efficiently inhibit production of NO, inhibit expression of iNOS and TNF-a, efficiently inhibit activities of COX-2 enzymes, exhibit excellent anti-inflammatory effects, and have little or no side effects or cytotoxicity and thus have almost no limit in terms of content because they are derived from natural substances.

In particular, at present, research and development associated with anti-inflammatory drugs as natural medicines using natural ingredients, or cosmetics or cosmetic components using natural ingredients in order to satisfy consumer demands are actively underway.

In addition, an anti-pyretic drug is a medicine which acts to lower fever, elevated body temperature, and is also referred to as an anti-pyretic and analgesic drug because it generally acts to alleviate both fever and pain.

Currently believed hypothesis regarding action mechanism associated with the anti-pyretic drug is that the anti-pyretic drug inhibits biosynthesis of prostaglandin (PG) and thereby alleviates fever and realizes anti-pyretic action.

Specifically, upon fever, prostaglandin levels in thermoregulatory centers of the hypothalamus increase. For this reason, fever activity is inhibited and anti-pyretic effect is thus obtained by reducing prostaglandin levels in the thermoregulatory centers. In addition, prostaglandin is a known pain-inducing mediator. However, a variety of mechanisms associated with fever symptoms have been suggested.

Currently prescribed anti-pyretic drugs include salicylic acid derivatives such as aspirin, aniline derivatives such as acetanilide and phenacetin, and pyrazolone derivatives such as antipyrine, aminopyrine or sulpyrine. In addition, among anti-inflammatory drugs, there are non-steroidal anti-inflammatory drugs having anti-pyretic and analgesic actions such as indomethacin.

As described above, correlation between anti-pyretic and analgesic actions and anti-inflammatory effects, that is, inflammation-alleviating effects, is often found. However, some drugs have no almost anti-inflammatory action, but have potent anti-pyretic action, whereas other drugs have almost no anti-pyretic action, but have potent anti-inflammatory effects. Therefore, anti-inflammatory effect is determined to be not necessarily directly related to anti-pyretic and analgesic effects.

Accordingly, there is a need for development of substances which are derived from natural substances, not chemicals causing problems involved in various side effects, such as aniline agents causing acute intoxication, exhibit superior anti-pyretic action and have almost no risk of the side effects or cytotoxicity because they are derived from natural substances.

In particular, at present, research and development associated with anti-inflammatory drugs as natural medicines using natural ingredients in order to satisfy consumer demands are actively underway.

SUMMARY OF THE INVENTION

Therefore, the present invention has been made in view of the above problems, and it is one object of the present invention to provide an anti-inflammatory composition, as an active ingredient, containing a plant extract which has a low probability of occurrence of problems associated with side effects.

It is another object of the present invention to provide an anti-pyretic composition containing, as an active ingredient, a plant extract which has a low probability of occurrence of problems associated with side effects.

In accordance with the present invention, the above and other objects can be accomplished by the provision of an anti-inflammatory composition comprising a *Stauntonia Hexaphylla* extract as an active ingredient. The anti-inflammatory composition may be a medical composition, for example, an anti-pyretic and analgesic drug. In addition, the anti-inflammatory composition may be provided as an active ingredient of a cosmetic composition for inhibiting inflammation.

In another aspect of the present invention, provided is an anti-inflammatory drug comprising a *Stauntonia Hexaphylla* extract as an active ingredient.

In another aspect of the present invention, provided is a cosmetic composition for relieving or alleviating inflammation, comprising a *Stauntonia Hexaphylla* extract as an active ingredient.

In another aspect of the present invention, provided is an anti-pyretic composition comprising a *Stauntonia Hexaphylla* extract as an active ingredient. The anti-pyretic composition may be a medical composition, for example, an anti-pyretic drug or an anti-pyretic and analgesic drug.

During research associated with naturally-derived anti-inflammation, the inventors of the present invention found that a *Stauntonia Hexaphylla* extract exhibits superior anti-inflammatory effects. More specifically, the *Stauntonia Hexaphylla* extract efficiently inhibits secretion of NO, suppresses expression of iNOS related to production of NO, and inhibits activities of cyclooxygenase (COX) enzymes which progress inflammatory response associated with biosynthesis of prostaglandin present in the body. In addition, it has been found that, among various solvent fractions of *Stauntonia Hexaphylla* leaf extracts, an ethyl acetate fraction efficiently inhibits both NO production and COX enzyme activity, as compared to other solvent fractions, so long as problems associated with toxicity are not generated.

In addition, during research associated with anti-inflammatory agents derived from natural substances, the inventors of the present invention found that a *Stauntonia Hexaphylla* extract exhibits superior anti-pyretic effects. More specifically, the *Stauntonia Hexaphylla* extract is found to have remarkably superior anti-pyretic effects, whereas other plant extracts having anti-inflammatory effects have no or almost no anti-pyretic effects. In addition, it has been found that, among various solvent fractions of *Stauntonia Hexaphylla* extracts, an ethyl acetate fraction exhibits superior anti-pyretic effects, as compared to other fractions, so long as problems associated with toxicity are not generated.

Hereinafter, the prevent invention will be described in more detail.

The present invention is directed to an anti-inflammatory composition comprising a *Stauntonia Hexaphylla* extract as an active ingredient.

*Stauntonia Hexaphylla* is a creeping evergreen plant of dicotyledonous ranales Lardizabalaceae, which is also called "*Stauntonia Hexaphylla* tree".

*Stauntonia Hexaphylla* is a monoecism. Leaves of *Stauntonia Hexaphylla* are alternate phyllotaxis and palmately compound leaves composed of five to seven small leaflets. Flowers of *Stauntonia Hexaphylla* bloom in May, are yellowish white in color and are racemous inflorescence. Fruits of *Stauntonia Hexaphylla* are egg-shaped or oval berries and have a length of 5 cm to 10 cm, ripen to reddish brown in October, and flesh thereof is more delicious than clematis berries. Seeds of *Stauntonia Hexaphylla* have an egg-like oval shape and are black in color. *Stauntonia Hexaphylla* is predominantly found in Korea, Japan, Taiwan or China. *Stauntonia Hexaphylla* is mainly grown in the valleys and woods in the south regions such as Jeollanam-do, Gyeongsangnam-do and Chungcheongnam-do in Korea.

The *Stauntonia Hexaphylla* extract may be produced in accordance with a common production method of plant extracts. For example, the *Stauntonia Hexaphylla* extract is produced by extracting fruits, flowers, leaves, branches, stems, roots or peels of *Stauntonia Hexaphylla*, or grains obtained by crushing these substances (hereinafter, simply referred to as "grains") preferably leaves of *Stauntonia Hexaphylla* or fruits of *Stauntonia Hexaphylla*, more preferably leaves of *Stauntonia Hexaphylla*, with an extraction solvent, or by extracting the same with an extraction solvent and then fractionating the resulting crude extracts with a fractionation solvent. Leaves of *Stauntonia Hexaphylla* are harvested in a great amount as compared to other sites thereof, are thus easy to produce and exhibit superior anti-inflammatory effects. Accordingly, the *Stauntonia Hexaphylla* extract is preferably a *Stauntonia Hexaphylla* leaf extract.

The extraction solvent may comprise at least one selected from the group consisting of water and organic solvents. The organic solvent may be a polar solvent such as alcohol having 1 to 5 carbon atoms, diluted alcohol, ethyl acetate or acetone, a non-polar solvent such as ether, chloroform, benzene, hexane or dichloromethane, or a mixture thereof. The alcohol having 1 to 5 carbon atoms may be methanol, ethanol, propanol, butanol, isopropanol or the like, but the present invention is not limited thereto. In addition, the diluted alcohol may be obtained by diluting alcohol with water at a concentration of 50% (v/v) to 99.9% (v/v).

The extraction solvent of the *Stauntonia Hexaphylla* extract preferably comprises at least one selected from the group consisting of water, alcohols having 1 to 5 carbon atoms, diluted alcohol and mixtures thereof, more preferably comprises at least one selected from the group consisting of water, alcohols having 1 to 4 carbon atoms and a mixture thereof, and even more preferably comprises water.

The extraction may be carried out 50° C. to 150° C., or 75° C. to 130° C., or 90° C. to 120° C., but the present invention is not limited thereto. In addition, the extraction time is not particularly limited, but may be 10 minutes to 12 hours, or 30 minutes to 6 hours, or 2 hours to 4 hours.

The *Stauntonia Hexaphylla* extract according to the present invention may be produced in accordance with a general method of producing plant extracts. Specifically, the method may be hot extraction including hot water extraction, cold-immersion extraction, warm-immersion extraction, ultrasonic extraction or the like and may be carried out using an ordinary extractor, ultrasonic extractor or fractionator.

In addition, the extract extracted with a solvent may then be subjected to fractionation using at least one solvent selected from the group consisting of hexane, chloroform, ethyl acetate, methylene chloride, ethyl ether, acetone, butanol, water and mixtures thereof. The solvent used for fractionation may be a combination of two or more types and may be used sequentially or in combination according to the polarity of solvent to prepare respective solvent extracts.

A fraction of the *Stauntonia Hexaphylla* extract is preferably an ethyl acetate fraction or a chloroform fraction, more preferably an ethyl acetate fraction.

The prepared extract or the fraction obtained by the fractionation process may then be subjected to filtration, concentration and/or drying to remove the solvent. Specifically, the filtration may be carried out using a filter paper or vacuum filter, the concentration may be carried out by vacuum-concentration using a vacuum concentrator, for example, a rotary evaporator, and the drying may be for example freeze-drying.

The *Stauntonia Hexaphylla* extract, for example, a *Stauntonia Hexaphylla* leaf hot water extract or a *Stauntonia Hexaphylla* fruit hot water extract is found to have no cytotoxicity even when treated at a concentration of 200 µg/Ml as a result of MTT analysis.

Accordingly, the anti-inflammatory composition may be used to inhibit inflammation, or to treat, relieve, alleviate or prevent inflammation.

The inflammation includes general inflammatory diseases and the inflammatory diseases for example include one or more selected from the group consisting of various chronic inflammatory diseases, such as various dermatitis including atopic dermatitis, dermatomyositis, polymyositis, allergies, systemic lupus erythematosus, pemphigus, aphthous stomatitis, retinitis, gastritis, hepatitis, bronchitis, esophagitis, colitis, pancreatitis, colitis, nephritis, decubitus, lupus, chronic thyroiditis and multiple sclerosis, various acute inflammatory diseases such as sepsis, shock, radiation injury and organ transplant rejection, generalized edema and localized edema.

Accordingly, the anti-inflammatory composition may be used to treat, prevent or relieve inflammatory diseases.

The allergies include anaphylaxis, allergic rhinitis, asthma, allergic conjunctivitis, allergic dermatitis, atopic dermatitis, contact dermatitis, urticaria, insect allergies, food allergies and medication allergies.

The generalized edema may specifically be selected from the group consisting of congestive heart failure, constrictive pericarditis, restrictive cardiomyopathy, liver cirrhosis, renal failure, nephrotic syndrome and a combination thereof. The localized edema is a swelling of a portion of skin and soft tissues, and specifically includes cellulitis accompanied with inflammation of the skin and soft tissues, drainage disorders of veins or lymphatic vessels, burns accompanied with partial loss of the skin and soft tissues, insect bites, and bacterial infection.

Accordingly, the anti-inflammatory composition of the present invention may be applied as a composition for treating or preventing inflammatory diseases, or a food composition for treating or preventing inflammatory diseases. The food composition is for example a health functional food composition for preventing or relieving inflammatory diseases.

The health functional food means a group of foods having added values provided by physical, biochemical and biotechnological methods so that the corresponding food performs or exerts intended functions suitable for specific applications, or a processed food to be designed so that a composition of the food sufficiently exhibits desired body modulation functions such as biological defense rhythm control, and disease prevention and restoration.

The health functional food may comprise a sitologically acceptable food auxiliary additive, and may further include a suitable carrier, excipient and diluent commonly used for preparation of health functional foods.

The health functional food composition for preventing or relieving inflammatory diseases according to the present invention may comprise the *Stauntonia Hexaphylla* extract in an amount of 0.001% by weight to 99.9% by weight or 0.01% by weight to 50% by weight or 0.1% by weight to 30% by weight or 0.1% by weight to 15% by weight, based on the total weight of the food.

The anti-inflammatory composition may be used as a drug ingredient or for medical or pharmaceutical applications. In this regard, the anti-inflammation composition may be a medical composition, for example, an anti-pyretic and analgesic drug.

The anti-inflammatory composition comprising the *Stauntonia Hexaphylla* extract as an active ingredient may be directly applied to animals including humans. The animals are a family of organisms, contrast to plants, which mainly intake organic matter as nutrients and are differentiated into digestive, excretory and respiratory organs, and are preferably mammals, more preferably humans.

The *Stauntonia Hexaphylla* extract may be used alone in the anti-inflammatory composition and may further comprise a pharmaceutically acceptable carrier, excipient, diluent or adjuvant. More specifically, when the composition comprising the *Stauntonia Hexaphylla* extract may be used as a drug ingredient or for medical or pharmaceutical applications, the *Stauntonia Hexaphylla* extract may be mixed with a pharmaceutically acceptable carrier or excipient or be diluted with a diluting agent in accordance with a general method before use.

In this case, a content of the *Stauntonia Hexaphylla* extract in the composition may be 0.001% by weight to 99.9% by weight, 0.1% by weight to 99% by weight or 1% by weight to 50% by weight, but the present invention is not limited thereto. The content of the extract may be controlled to a reasonable level according to usage form and method of the composition.

Examples of the pharmaceutically acceptable carrier, excipient or diluent include, but are not limited to, one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, dextrin, calcium carbonate, propylene glycol, liquid paraffin, and physiological saline, but any ordinary carrier, excipient or diluent may be used without limitation to these substances. In addition, the pharmaceutical composition may further comprise ordinary fillers, extenders, binders, disintegrating agents, anti-agglutinating agents, lubricating agents, wetting agents, pH control agents, nutrients, vitamins, electrolytes, alginic acid and salts thereof, pectic acid and salts thereof, protective colloids, glycerin, flavoring agents, emulsifiers or preservatives. These ingredients may be added singly or in combination to the *Stauntonia Hexaphylla* extract, the active ingredient.

In addition, the composition of the present invention may further comprise, in addition to the active ingredient, well-known substances determined to have anti-inflammatory effects, for example, substances used as COX-2 inhibitors, NO inhibitors or anti-inflammatory drugs.

The composition may be administered orally or parenterally when used as a drug ingredient and the composition may be, for example, administered through various routes including oral, transdermal, subcutaneous, intravenous and muscular routes.

In addition, a formulation of the composition may be varied according to usage form and the composition may be formulated by a method well-known in the art so that the active ingredient is rapidly, sustained or delayed released after administration to a mammalian animal. Generally, solid preparations for oral administration include tablets, caplets, soft or hard capsules, pills, powders, granules and the like. These preparations may be, for example, prepared by mixing one or more excipients, such as starch, calcium carbonate, sucrose, lactose and gelatin. In addition, in addition to a simple excipient, lubricants such as magnesium stearate or talc may also be used. Liquid preparations for oral administration include suspensions, liquids and solutions for internal use, emulsions, syrups and the like. The liquid preparations may comprise various excipients, for example, wetting agents, sweeting agents, flavoring agents and preservatives, in addition to water and liquid paraffin which are commonly used simple diluents.

Preparations for parenteral administration include creams, lotions, ointments, plasters, liquids and solutions, aerosols, fluid extracts, elixirs, infusions, sachets, patches, injections and the like.

Furthermore, the composition of the present invention may be formulated using a reasonable method well-known in the art to which the present invention pertains or a method described in the Remington's Pharmaceutical Science (recent edition, Mack Publishing Company, Easton Pa.).

Dose of the composition may be determined in consideration of dosage method, age and sex of takers, severity and conditions patients, intake of active ingredient in the body, inactivation ratio and drugs used in conjunction therewith. The dose may be for example 0.1 mg/kg (body weight) to 500 mg/kg (body weight), 0.1 mg/kg (body weight) to 400 mg/kg (body weight) or 1 mg/kg (body weight) to 300 mg/kg (body weight), based on the active ingredient per day. The composition may be administered once or in several portions. The dose is not construed as limiting the scope of the present invention in any aspect.

In addition, the present invention provides an anti-inflammatory composition comprising the *Stauntonia Hexaphylla* extract as an active ingredient.

In addition, the present invention provides an anti-inflammatory drug comprising the *Stauntonia Hexaphylla* extract as an active ingredient.

The *Stauntonia Hexaphylla* extract is preferably a *Stauntonia Hexaphylla* leaf hot water extract, more preferably an ethyl acetate fraction of a *Stauntonia Hexaphylla* leaf hot water extract.

The anti-inflammatory drug may comprise the active ingredient alone and may further comprise a pharmaceutically acceptable carrier or excipient according to formulation, usage form and usage purpose. When the anti-inflammatory drug is provided as a mixture, the active ingredient may be present in an amount of 0.1% by weight to 99.9% by weight, with respect to the total weight of the anti-inflammatory drug, but is generally present in an amount of 0.001% by weight to 50% by weight.

The anti-inflammatory drug may be used for preventing and treating various chronic inflammatory diseases such as lupus and multiple sclerosis, various acute inflammatory diseases such as sepsis, shock, radiation injury and organ transplant rejection, ophthalmologic diseases, bronchitis, or inflammatory bowel diseases.

Examples of the carrier or excipient include, but are not limited to, water, dextrin, calcium carbonate, lactose, propylene glycol, liquid paraffin, physiological saline, dextrose, sucrose, sorbitol, mannitol, xylitol, erythritol, maltitol, starch, gelatin, calcium phosphate, calcium silicate, cellulose, methyl cellulose, polyvinyl pyrrolidone, methyl hydroxybenzoate, propyl hydroxybenzoate, talc, magnesium stearate and mineral oil. The carrier or excipient may be used in combination of two or more types.

In addition, when the anti-inflammatory drug is provided as a medicine, the medicine may further comprise ordinary fillers, extenders, binders, disintegrating agents, surfactants, anti-agglutinating agents, lubricating agents, wetting agents, flavorings, emulsifiers, preservatives or the like.

In addition, the anti-inflammatory drug of the present invention may further comprise, in addition to the active ingredient, a well-known compound or plant extract having anti-inflammatory activity, and the compound or the plant extract may be present in an amount of 0.1 parts by weight to 99.9 parts by weight or 0.5 parts by weight to 20 parts by weight, with respect to 100 parts by weight of the active ingredient.

The anti-inflammatory drug may be formulated into a suitable form determined according to usage form and in particular, may be formulated by a method well-known in the art so that the active ingredient is rapidly, sustained or delayed released after administration to a mammalian animal. Specifically, examples of the formulation include plasters, granules, lotions, liniments, limonages, powders, syrups, eye ointments, liquids and solutions, aerosols, extracts, elixirs, ointments, fluidextracts, emulsions, suspensions, decoctions, infusions, eye drops, tablets, suppositories, injections, spirits, capsules, creams, pills, soft or hard gelatin capsules and the like.

The anti-inflammatory drug according to the present invention may be administered orally or parenterally and may be, for example, used through dermal, intramuscular, intraperitoneal, intravenous, subcutaneous, nasal, epidural and oral routes. The dose may be determined in consideration of dosage method, age, sex and body weight of takers, severity of diseases and the like. For example, the anti-inflammatory drug of the present invention may be administered one or more times in a daily dose of 0.1 mg/kg (body weight) to 100 mg/kg (body weight), based on the active ingredient. However, the dose is provided only as an example and the present invention is not limited thereto.

In addition, the present invention provides a cosmetic composition comprising the *Stauntonia Hexaphylla* extract as an active ingredient.

The *Stauntonia Hexaphylla* extract is free of both problems associated with side effects because it is derived from a natural substance, has no cytotoxicity, and efficiently regulates inflammation induced by ingredients contained in cosmetics and inflammation induced by external environments due to potent inflammation-inhibitory effect and thus superior anti-inflammatory and anti-irritant activities. Accordingly, the *Stauntonia Hexaphylla* extract may be used as an active ingredient of the cosmetic composition having the effects of relieving, preventing and alleviating inflammation. In this regard, the cosmetic composition may be a cosmetic composition for relieving or alleviating inflammation.

The *Stauntonia Hexaphylla* extract is preferably a *Stauntonia Hexaphylla* leaf hot water extract, more preferably an ethyl acetate fraction of a *Stauntonia Hexaphylla* hot water extract.

The cosmetic composition may be utilized in applications including skin-care cosmetics, make-up cosmetics, body cosmetics, hair cosmetics, scalp cosmetics, shaving cosmetics or oral cosmetics.

Examples of the skin-care cosmetics include creams, lotions, packs, massage creams, emulsions and the like, examples of the makeup cosmetics include foundations, makeup bases, lipsticks, eye shadows, eyeliners, mascaras, eyebrow pencils and the like, and examples of body cosmetics include soaps, liquid detergents, bath preparations, sunscreen creams, sunscreen oils and the like. Examples of the hair cosmetics include hair shampoos, conditioners, hair treatments, hair mousse, hair liquids, pomade, hair colors, hair bleaches, color rinses and the like, and examples of the scalp cosmetics include hair tonics, scalp treatments or the like. Examples of the shaving cosmetics include aftershave lotions or shaving creams and examples of the oral cosmetics include toothpaste, mouth washes and the like.

In addition to the active ingredient, ingredients commonly blended with cosmetic compositions, for example, humectants, UV absorbers, vitamins, animal and plant extracts, digesters, whitening agents, vasodilators, astringents, refreshing agents and hormone drugs, may be further blended with the cosmetic composition, according to intended use and properties of the cosmetic composition. In addition, the cosmetic composition may further comprise a base ingredient to permeate or migrate the drug or the active ingredient into skin tissues.

The formulation of the cosmetic composition may be provided as a suitable form according to intended use and properties of the cosmetic composition and examples of the formulation include aqueous solutions, solubilizing agents, emulsions, oils, gels, pastes, ointments, aerosols, water-oil di-layer systems or water-oil-powder tri-layer systems. The examples of the formulation are provided only for exemplification and are not construed as limiting the formulation and form of the cosmetic composition of the present invention.

The active ingredient may be present in an amount of 0.001% by weight to 50% by weight, preferably 0.01% by weight to 20% by weight, based on the total weight of the cosmetic composition, but the content may be suitably controlled according to contents of ingredients, other than the active ingredient, contained in the formulation or the cosmetic composition, and is not construed as limiting the content of the active ingredient according to the present invention.

The present invention is directed to an anti-pyretic composition comprising a *Stauntonia Hexaphylla* extract as an active ingredient.

The *Stauntonia Hexaphylla* extract may be produced in accordance with a common production method of plant extracts. For example, the *Stauntonia Hexaphylla* extract is produced by extracting leaves, branches, stems, roots or peels of *Stauntonia Hexaphylla*, or grains obtained by crushing these substances (hereinafter, simply referred to as "grains"), preferably leaves of *Stauntonia Hexaphylla*, with an extraction solvent, or by extracting the same with an extraction solvent and then fractionating the resulting crude extract with a fractionation solvent.

Leaves of *Stauntonia Hexaphylla* are harvested in a great amount as compared to other sites thereof, are thus easy to produce and exhibit superior anti-inflammatory effects. Accordingly, the *Stauntonia Hexaphylla* extract is preferably a *Stauntonia Hexaphylla* leaf extract.

The extraction solvent may comprise at least one selected from the group consisting of water and organic solvents. The organic solvent may be a polar solvent such as alcohol having 1 to 5 carbon atoms, diluted alcohol, ethyl acetate or acetone, a non-polar solvent such as ether, chloroform, benzene, hexane or dichloromethane, or a mixture thereof.

The extraction solvent of the *Stauntonia Hexaphylla* extract preferably comprises at least one selected from the group consisting of water, alcohols having 1 to 5 carbon atoms, diluted alcohol and mixtures thereof, more preferably comprises any one selected from the group consisting of water, alcohols having 1 to 4 carbon atoms and a mixture thereof, and even more preferably comprises water. The extraction may be carried out 50° C. to 150° C., or 75° C. to 120° C., or 90° C. to 115° C., but the present invention is not limited thereto. In addition, the extraction time is not particularly limited, but may be 10 minutes to 12 hours, or 30 minutes to 8 hours, or 2 hours to 6 hours.

The *Stauntonia Hexaphylla* leaf extract according to the present invention may be produced in accordance with a general method of producing plant extracts. Specifically, the method may be hot extraction including hot water extraction, cold-immersion extraction, warm-immersion extraction, ultrasonic extraction or the like and may be carried out using an ordinary extractor, ultrasonic extractor or fractionator.

In addition, the extract extracted with a solvent may then be subjected to fractionation using at least one solvent selected from the group consisting of hexane, chloroform, methylene chloride, ethyl acetate, ethyl ether, acetone, butanol, water and mixtures thereof. The solvent used for fractionation may be a combination of two or more types and may be used sequentially or in combination according to the polarity of solvent to prepare respective solvent extracts.

A fraction of the prepared *Stauntonia Hexaphylla* solvent extract, specifically, a fraction of the *Stauntonia Hexaphylla* leaf hot water extract is preferably an ethyl acetate fraction, a chloroform fraction or a butanol fraction, more preferably an ethyl acetate fraction or a chloroform fraction, even more preferably, an ethyl acetate fraction.

The prepared extract or the fraction obtained by the fractionation process may then be subjected to filtration, concentration and/or drying to remove the solvent. Specifically, the filtration may be carried out using a filter paper or vacuum filter, the concentration may be carried out by vacuum-concentration using a vacuum concentrator, for example, a rotary evaporator, and the drying may be for example freeze-drying.

The anti-pyretic composition may be used as a drug or for medical or pharmaceutical applications. In this regard, the anti-pyretic composition may be a medical composition, for example, an anti-pyretic drug, or an anti-pyretic and analgesic drug.

When the anti-pyretic composition is used for medical or pharmaceutical applications, the anti-pyretic composition may be used for inhibiting abnormal generated heat (fever) or treating or preventing abnormal fever accompanied by diseases.

In this regard, the present invention is directed to an anti-pyretic composition comprising the *Stauntonia Hexaphylla* extract as an active ingredient. The anti-pyretic composition comprising the *Stauntonia Hexaphylla* extract, preferably, the *Stauntonia Hexaphylla* leaf extract, as an active ingredient, may be used for inhibiting, treating, relieving or preventing abnormal fever or abnormal fever accompanied by diseases or disorders and may be specifically an anti-pyretic and analgesic drug.

Regarding the anti-pyretic composition comprising the *Stauntonia Hexaphylla* extract as an active ingredient, the *Stauntonia Hexaphylla* extract is a *Stauntonia Hexaphylla* leaf extract, preferably a chloroform fraction, an ethyl acetate fraction or a butanol fraction of the *Stauntonia Hexaphylla* leaf extract, more preferably, an ethyl acetate fraction or a chloroform fraction of the *Stauntonia Hexaphylla* leaf extract, even more preferably an ethyl acetate fraction of the *Stauntonia Hexaphylla* leaf extract.

The abnormal fever means an abnormally high body temperature.

The anti-pyretic drug is used to eliminate abnormal fever and refers to a medicine used to lower an abnormally elevated body temperature to a reasonable level. Previously reported anti-pyretic drugs include antipyrin, antifebrin, aspirin, salipyrin and the like. The anti-pyretic drug is also called an "anti-pyretic and analgesic drug" because it generally has the effect of alleviating pain.

The anti-pyretic composition comprising the *Stauntonia Hexaphylla* extract as an active ingredient may be directly applied to animals including humans. The animals are a family of organisms, contrast to plants, which mainly intake organic matter as nutrients and are differentiated into digestive, excretory and respiratory organs, and are preferably mammals, more preferably humans.

The *Stauntonia Hexaphylla* extract may be used alone in the anti-pyretic composition and a pharmaceutically acceptable carrier, excipient, diluent or adjuvant may further added.

More specifically, when the composition comprising the *Stauntonia Hexaphylla* extract may be used as a drug or for medical or pharmaceutical applications, the *Stauntonia Hexaphylla* extract may be mixed with a pharmaceutically acceptable carrier or excipient or be diluted with a diluting agent in accordance with a general method before use.

In this case, a content of the *Stauntonia Hexaphylla* extract in the composition may be 0.001% by weight to 99.9% by weight, 0.1% by weight to 99% by weight or 1% by weight to 50% by weight, but the present invention is not limited thereto. The content of the extract may be controlled to a reasonable level according to usage form and method of the composition.

Examples of the pharmaceutically acceptable carrier, excipient or diluent include, but are not limited to, one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, dextrin, calcium carbonate, propylene glycol, liquid paraffin, and physiological saline, but any ordinary carrier, excipient or diluent may be used without limitation to these substances. The carrier or the excipient may be used in combination of two or more types.

In addition, the anti-pyretic composition may further comprise ordinary fillers, extenders, binders, disintegrating agents, anti-agglutinating agents, lubricating agents, wetting agents, pH control agents, nutrients, vitamins, electrolytes, alginic acid and salts thereof, pectic acid and salts thereof, protective colloids, glycerin, flavoring agents, emulsifiers or preservatives. These ingredients may be added singly or in combination to the *Stauntonia Hexaphylla* extract, the active ingredient.

In addition, the anti-pyretic composition may further comprise, in addition to the active ingredient, a well-known substance considered to have anti-pyretic effect.

In addition, the anti-pyretic drug may further comprise, in addition to the active ingredient, a well-known compound or plant extract considered to have anti-pyretic effect and may be present in an amount of 0.1 parts by weight to 99.9 parts by weight or 0.5 parts by weight to 20 parts by weight, based on 100 parts by weight of the active ingredient.

The composition may be administered orally or parenterally when used for a drug and the composition may be, for example, administered through various routes including oral, transdermal, subcutaneous, intravenous and muscular routes.

In addition, a formulation of the composition may be varied according to usage form and the composition may be formulated by a method well-known in the art so that the active ingredient is rapidly, sustained or delayed released after administration to a mammalian animal.

Generally, solid preparations for oral administration include tablets, caplets, soft or hard capsules, pills, powders, granules and the like. These preparations may be, for example, prepared by mixing one or more excipients, such as starch, calcium carbonate, sucrose, lactose and gelatin. In addition, in addition to a simple excipient, lubricants such as magnesium stearate or talc may also be used. Liquid preparations for oral administration include suspensions, liquids and solutions for internal use, emulsions, syrups and the like. The liquid preparations may comprise various excipients, for example, wetting agents, sweeting agents, flavoring agents and preservatives, in addition to water and liquid paraffin which are commonly used simple diluents.

Preparations for parenteral administration include creams, lotions, ointments, plasters, liquids and solutions, aerosols, fluid extracts, elixirs, infusions, sachets, patches, injections and the like.

Furthermore, the composition of the present invention may be formulated using a reasonable method well-known in the art to which the present invention pertains or a method described in the Remington's Pharmaceutical Science (recent edition, Mack Publishing Company, Easton Pa.).

Dose of the composition may be determined in consideration of dosage method, age and sex of takers, severity and conditions of patients, intake of active ingredient in the body, inactivation ratio and drugs used in conjunction therewith. The dose may be for example 0.1 mg/kg (body weight) to 500 mg/kg (body weight), 0.1 mg/kg (body weight) to 400 mg/kg (body weight) or 1 mg/kg (body weight) to 300 mg/kg (body weight), based on the active ingredient per day. The composition may be administered once or in several portions. The dose is not construed as limiting the scope of the present invention in any aspect.

Advantageous Effects

The *Stauntonia Hexaphylla* extract of the present invention is an edible plant-derived extract, is free of problems associated with side effects and safety, is determined to have considerably low cytotoxicity as a result of MTT analysis and exhibits anti-inflammatory and anti-pyretic effects, thus being used for medicines or cosmetics requiring anti-inflammatory effects and medications requiring anti-pyretic effects.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, configurations and effects of the present invention will be described in more detail with reference to specific examples and comparative examples for better understating of the present invention. The following examples are provided only for clear understanding only and should not be construed as limiting the scope and spirit of the present invention. The scope of the present invention to be protected should be interpreted by the claims and all technical concepts equivalent thereto fall within the scope of the present invention to be protected.

Example 1

Preparation of *Stauntonia Hexaphylla* Extract and Fraction 1-1. Preparation of *Stauntonia Hexaphylla* Extract A *Stauntonia Hexaphylla* leaf hot water extract was prepared at 110° C. using hot water and 10 kg of a *Stauntonia Hexaphylla* leaf in accordance with a hot water extraction method illustrated in FIG. 1. In addition, a *Stauntonia Hexaphylla* fruit hot water extract was prepared at 100° C. using 40 L of hot water and 2,100 g of a *Stauntonia Hexaphylla* fruit in accordance with a hot water extraction method described in FIG. 2.

More specifically, 200 L of distilled water was added to 10 kg of a *Stauntonia Hexaphylla* leaf washed with distilled water, and hot water extraction was then performed while heating the resulting mixture in an electric medicine boiling pot at 100° C. for 3 hours. In addition, 40 L of distilled water was added to 2,100 g of a *Stauntonia Hexaphylla* fruit washed with distilled water, and hot water extraction was then performed while heating the resulting mixture in an electric medicine boiling pot at 100° C. for 3 hours.

After the extraction, each extract was filtered through a 400 mesh filter cloth and the resulting filtrate was concentrated using a vacuum rotary concentrator. The residue left after the filtration was extracted, filtered and concentrated under vacuum two more times in the same manner as above using the equivalent amount of distilled water.

The *Stauntonia Hexaphylla* leaf hot water extract and the *Stauntonia Hexaphylla* fruit hot water extract prepared by the process were freeze-dried using a freeze-dryer. 1 kg of the *Stauntonia Hexaphylla* leaf hot water extract was obtained through the freeze-drying. As a result, a yield obtained by the *Stauntonia Hexaphylla* leaf hot water extraction was determined to be 10%. In addition, 148 g of the *Stauntonia Hexaphylla* fruit hot water extract was obtained through the freeze-drying. As a result, a yield obtained by the *Stauntonia Hexaphylla* fruit hot water extraction was determined to be 7%.

1-2. Preparation of Fractions of *Stauntonia Hexaphylla* Extract

Figure 1:
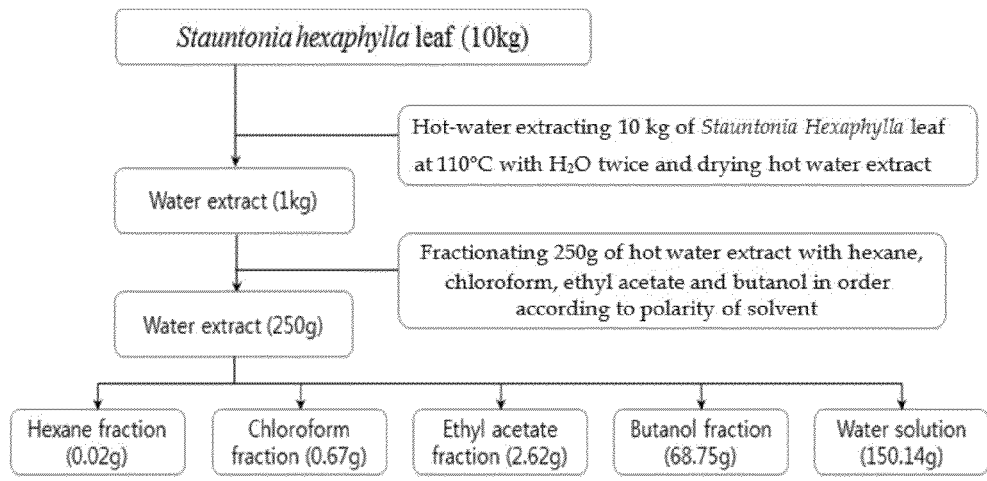
FIG. 1 is a schematic diagram illustrating a process of preparing a *Stauntonia Hexaphylla* leaf hot water extract and solvent fractions thereof according to an embodiment of the present invention.
Figure 2:
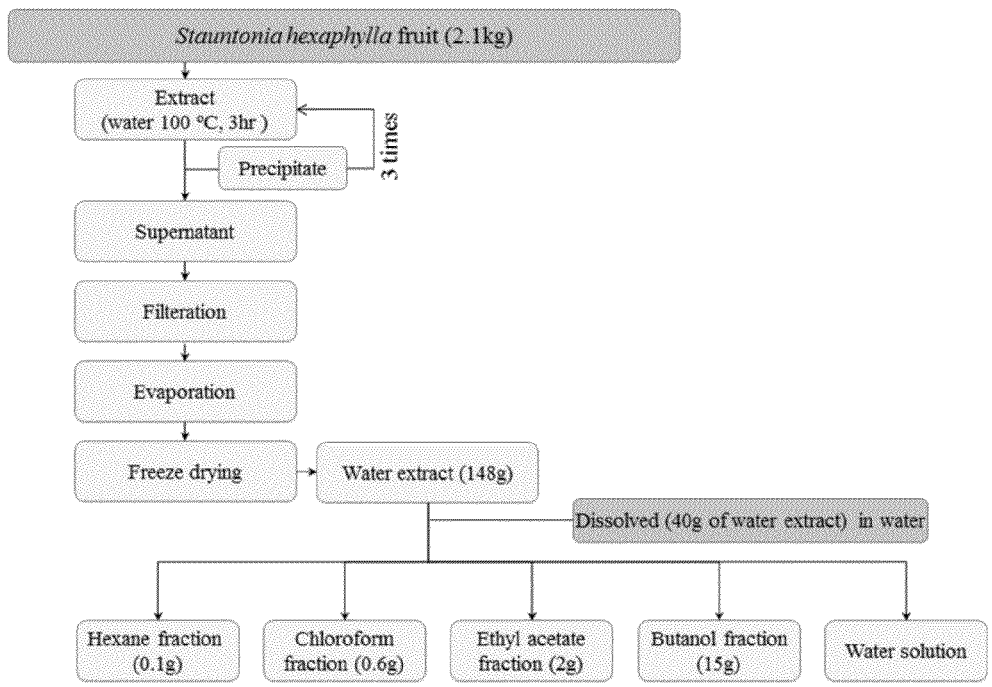
FIG. 2 is a schematic diagram illustrating a process of preparing a *Stauntonia Hexaphylla* fruit hot water extract and solvent fractions thereof according to an embodiment of the present invention.

Fractions of the *Stauntonia Hexaphylla* leaf hot water extract and the *Stauntonia Hexaphylla* fruit hot water extract were prepared in accordance with the method illustrated in FIG. 1 or 2.

Specifically, 250 g of the *Stauntonia Hexaphylla* leaf hot water extract was thoroughly dissolved in 5 L of distilled water, the resulting solution was charged in a fractionating column and 5 L of hexane was added thereto, followed by mixing and fractionation to separate a hexane layer as a hexane-soluble layer from an aqueous layer as a hexane-insoluble layer. The hexane layer was collected to prepare a hexane fraction solution.

5 L of chloroform was added to the remaining solution (aqueous layer), followed by mixing and fractionation, to separate a chloroform layer as a chloroform-soluble layer and an aqueous layer as a chloroform-insoluble layer. The chloroform layer was collected to prepare a chloroform fraction solution.

5 L of ethyl acetate was added to the remaining solution (aqueous layer), followed by mixing and fractionation, to separate an ethyl acetate layer as an ethyl acetate-soluble layer and an aqueous layer as an ethyl acetate-insoluble layer. The ethyl acetate layer was collected to prepare an ethyl acetate fraction solution.

5 L of butanol was added to the remaining solution (aqueous layer), followed by mixing and fractionation, to separate a butanol layer as a butanol-soluble layer and an aqueous layer as a butanol-insoluble layer. The butanol layer was collected to prepare a butanol fraction solution.

The butanol-insoluble layer left after fractionation and separation of the butanol-soluble layer was concentrated to remove the remaining organic solvent, thereby preparing a water fraction solution.

The respective fraction solutions thus obtained were filtered in a vacuum filtration system, concentrated and freeze-dried at −20° C. to completely remove the solvents, which were used for the present experiment. Through the process, 0.02 g of a hexane fraction (0.015%), 0.67 g of a chloroform fraction (0.27%), 2 g of an ethyl acetate fraction (1.05%) and 68.75 g of a butanol fraction (27.5%) were obtained and used as samples.

In the preparation process, the hexane fraction was found to be unsuitable for use because it might cause problems associated with industrial processes due to excessively low yield. The obtained extracts and fractions were freeze-stored until they were used for experiments. In addition, the butanol and water fractions were found to have high yield, and economic efficiency and industrial applicability were thus considered to be excellent due to high fraction yields.

In addition, a fraction of the *Stauntonia Hexaphylla* fruit hot water extract was prepared by a method including completely dissolving 40 g of the *Stauntonia Hexaphylla* fruit hot water extract in 1 L of distilled water, respectively adding 1 L of fractionation solvents, that is, hexane, chloroform, ethyl acetate and butanol in a fractionating column in the same manner as above, followed by mixing and fractionation, thereby separating the solvent-soluble layers.

The fraction solutions of the *Stauntonia Hexaphylla* fruit hot water extract thus obtained were filtered in a vacuum filtration system, concentrated and freeze-dried at −20° C. to completely remove the solvents, which were then used in the present experiments. Through the process, 0.1 g of a hexane fraction, 0.6 g of a chloroform fraction, 2 g of an ethyl acetate fraction and 15 g of a butanol fraction were obtained and used as samples.

Example 2

Cytotoxicity Test of Extracts and Fractions

To determine cytotoxicity of the *Stauntonia Hexaphylla* leaf hot water extract, the *Stauntonia Hexaphylla* fruit hot water extract and the *Stauntonia Hexaphylla* leaf hot water extract fraction prepared in Example 1, mouse macrophage primary cells, RAW264.7 cells available from ATCC were used.

DMEM/F12 (Dulbecco's modified Eagle's medium/Nutrient Mixture Ham's F12), FBS (fetal bovine serum), L-glutamine and penicillin-streptomycin used for culturing the cells were obtained from Gibco/BRL (USA).

The RAW264.7 cells were cultured in a DMEM/F12 medium supplemented with 10% FBS, 1% penicillin-streptomycin and 1% L-glutamine and incubated at 37° C. and at a predetermined humidity in a $CO_2$ incubator (5% $CO_2$/95% air).

The cells were cultured to a confluence of about 80% on a culture dish, and a monolayer of the cells was rinsed with PBS (pH 7.4) and then washed. Then, the cells were treated with 0.25% trypsin and 2.56 mmol/L of EDTA and were then passage-cultured. The cells were fed with a fresh medium every two days.

The cultured cells were seeded on a 48 well-plate at a density of 50,000 cells/well and further cultured for 24 hours. After 24 hours, a control group treated with only LPS, without treating with any sample, and experimental groups treated with LPS and solutions of the *Stauntonia Hexaphylla* leaf extracts and fractions thereof obtained in Example 1 prepared at different concentrations in DMSO which had been determined not to have any effect on cell viability were further cultured for 24 hours, the culture solutions were removed and the number of viable cells was measured by MTT assay. MTT assay was performed by the following method.

First, the cell culture medium was removed, each well was treated with 1 mL of a DMEM/F12 medium containing 1 mg/mL of MTT and the cells were further cultured at 37° C. and a predetermined humidity in a $CO_2$ incubator for 4 hours. After removing the medium, a tetrazolium bromide salt was removed, formazan crystals produced in each well were dissolved in 200 µl of DMSO, and absorbance at a wavelength of 540 nm was measured in a microplate reader (BIO-RAD) to determine cell viability.

Figure 3:
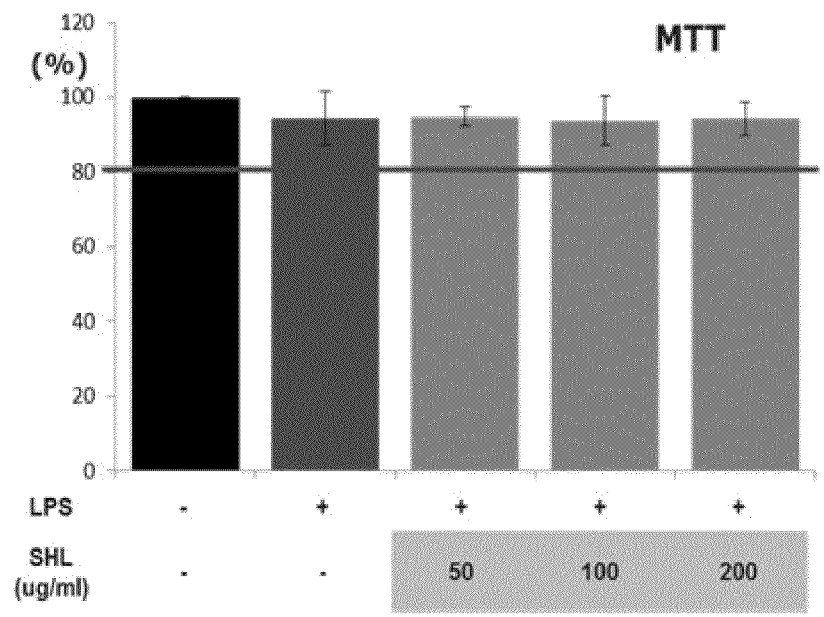
FIG. 3 is a graph showing measurement results of cytotoxicity of the *Stauntonia Hexaphylla* leaf extract using RAW264.7 cell lines by MTT assay according to an embodiment of the present invention, wherein + means treated with LPS (1 μg/Ml) or the extract, − means non-treated, an SHL value of a horizontal axis represents a dose (μg/Ml) of the *Stauntonia Hexaphylla* leaf hot water extract and a vertical axis represents relative cytotoxicity (%) as compared to a control group not-treated with any sample.
Figure 4:
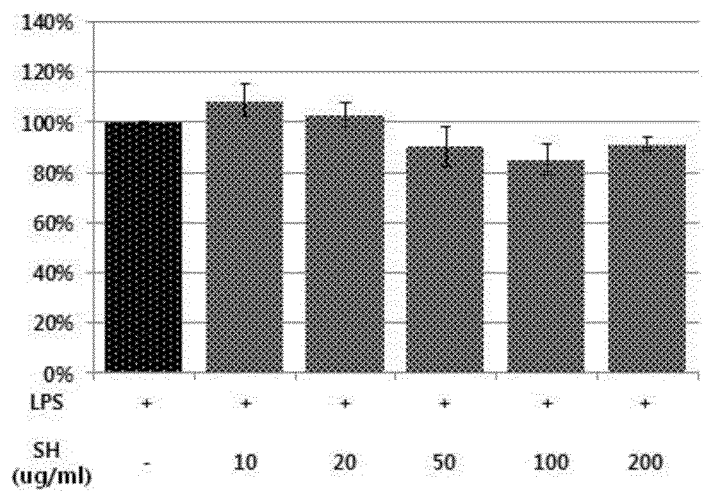
FIG. 4 is a graph showing measurement results of cytotoxicity of the *Stauntonia Hexaphylla* fruit extract using RAW264.7 cell lines by MTT assay according to an embodiment of the present invention, wherein + means treated with LPS (1 μg/MB) or the extract, − means non-treated, an SH value of a vertical axis represents a dose (μg/Ml) of the *Stauntonia Hexaphylla* fruit hot water extract.

Results of treatment with the *Stauntonia Hexaphylla* leaf extract were expressed as means of measured values obtained by repeating the test three times and are shown in FIG. 3. Results of treatment with the *Stauntonia Hexaphylla* fruit extract were expressed as means of measured values obtained by repeating the test three times and are shown in FIG. 4. Results of treatment with the fraction of the *Stauntonia Hexaphylla* leaf hot water extract were expressed as means of measured values obtained by repeating the test three times and are shown in FIG. 10.

As can be seen from FIG. 3, all groups treated with the *Stauntonia Hexaphylla* leaf hot water extract prepared in Example 1-1 at different concentrations, specifically, at different concentrations ranging from 50 µg/Ml to 200 µg/Ml, had no effects on cell proliferation even after 24 hours, as compared to the control group treated with only LPS, without treating with any sample. From the results, it was determined that the *Stauntonia Hexaphylla* leaf extract had no cytotoxicity at a concentration of less than or equal to 200 µg/Ml.

In addition, as can be seen from FIG. 4, as a result of comparison between groups treated with the *Stauntonia Hexaphylla* fruit extract prepared in Example 1-1 at different concentrations, specifically, at different concentrations ranging from 50 µg/Ml to 200 µg/Ml, for 24 hours, and the control group treated with only LPS, without treating with any sample, all treated groups had no effects on cell proliferation. From the results, it was determined that the *Stauntonia Hexaphylla* fruit extract had no cytotoxicity at a concentration of less than or equivalent to 200 µg/Ml.

Figure 10:
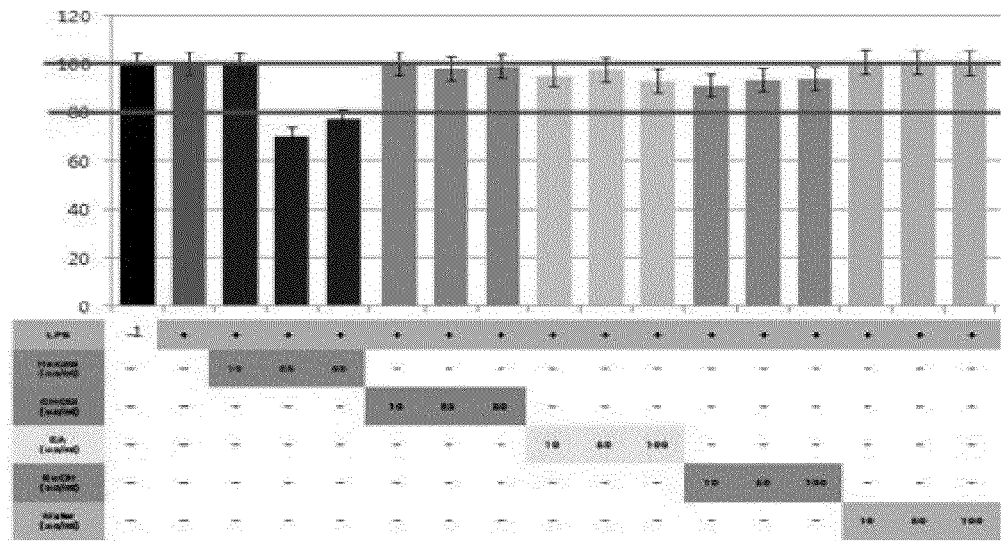
FIG. 10 is a graph showing cytotoxicity of the *Stauntonia Hexaphylla* leaf hot water extract measured by MTT assay using RAW264.7 cell lines according to an embodiment of the present invention, wherein + means treated with LPS (1 μg/Ml) or a solvent fraction, − means not treated with any sample, values of a horizontal axis represents doses (μg/Ml) of different solvent fractions of the *Stauntonia Hexaphylla* leaf hot water extract and a vertical axis represents cytotoxicity (%) as compared to a control group not treated with any sample.

In addition, as can be seen from FIG. 10, in case of the fractions of the *Stauntonia Hexaphylla* leaf hot water extract prepared in Example 1-2, an experimental group treated with 25 µg/Ml of the hexane fraction exhibited a significant decrease in cell viability, which demonstrated that the experimental group had cytotoxicity. In addition, an experimental group treated with 100 µg/Ml of the ethyl acetate fraction exhibited an insignificant and slight decrease in cell viability, whereas an experimental group treated with 200 µg/Ml of the ethyl acetate fraction exhibited a significant decrease in cell viability, which demonstrated that the ethyl acetate fraction was safe at a concentration of less than or equal to 100 µg/Ml. In case of other solvent fractions, cell viability was maintained at 50 µg/Ml or 100 µg/Ml, and fractions using solvents other than hexane, as fractionation solvents, had no cytotoxicity and were safe, when treated with the extract at a concentration of 50 µg/Ml.

Example 3

Determination of Anti-Inflammatory Effect of *Stauntonia Hexaphylla* Leaf Extract and Fraction Thereof The RAW 264.7 cells cultured in Example 2 were used to determine anti-inflammatory effect of the *Stauntonia Hexaphylla* leaf extract and fractions thereof prepared in Example 1.

The cells were treated with the *Stauntonia Hexaphylla* leaf hot water extract or solvent fractions thereof prepared in Example 1, together with LPS, and cultured for 24 hours in the same manner as in Example 2. The cultured solution was centrifuged at 3,000 rpm for 5 minutes and a supernatant was separated. The supernatant was treated and reacted with an equal amount of Griess reagent (1% sulfanilamide, 0.1% naphthyl-ethylene diamine dihydrochloride, 2% phosphoric acid, Promega, USA), and NO secretion was measured at 540 nm. The results are shown in FIGS. 5 and 11.

Figure 5:
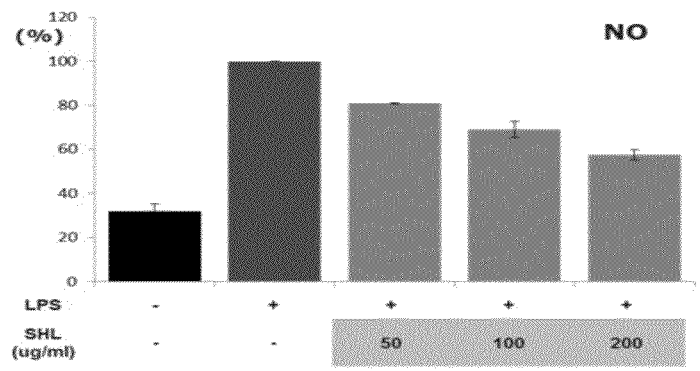
FIG. 5 is a graph showing NO secretion measured to determine anti-inflammatory effects of the *Stauntonia Hexaphylla* leaf hot water extract using RAW264.7 cell lines according to an embodiment of the present invention, wherein + means treated together with LPS (1 μg/Ml), − means non-treated with LPS (1 μg/Ml), an SHL value of a horizontal axis represents a dose (μg/Ml) of the *Stauntonia Hexaphylla* leaf hot water extract and a vertical axis represents relative NO secretion (%) as compared to a control group treated only with LPS.

As can be seen from FIG. 5, a control group not treated with LPS was found to exhibit low NO secretion. On the other hand, an experimental group treated with LPS was found to exhibit a prominent increase in NO secretion due to inflammation induced by LPS. In addition, in spite of treatment with LPS, groups treated with the *Stauntonia Hexaphylla* leaf hot water extract prepared in Example 1 exhibited a concentration-dependent decrease in NO secretion. In particular, a group treated with 100 µg/Ml of the *Stauntonia Hexaphylla* leaf hot water extract decreased NO secretion to 80% of the control group inflammation-induced by LPS, a group treated with 200 μg/Ml of the *Stauntonia Hexaphylla* leaf hot water extract decreased NO secretion to about 70% of the control group inflammation-induced by LPS, which demonstrated that the *Stauntonia Hexaphylla* leaf extract had anti-inflammatory effects.

The *Stauntonia Hexaphylla* leaf hot water extract had no effect on cell survival and was thus determined to have no cytotoxicity, when it was treated at a concentration of 200 μg/Ml in Example 2. Accordingly, the *Stauntonia Hexaphylla* leaf extract was determined to have no cytotoxicity, be safe and exhibit superior anti-inflammatory effect.

Figure 11:
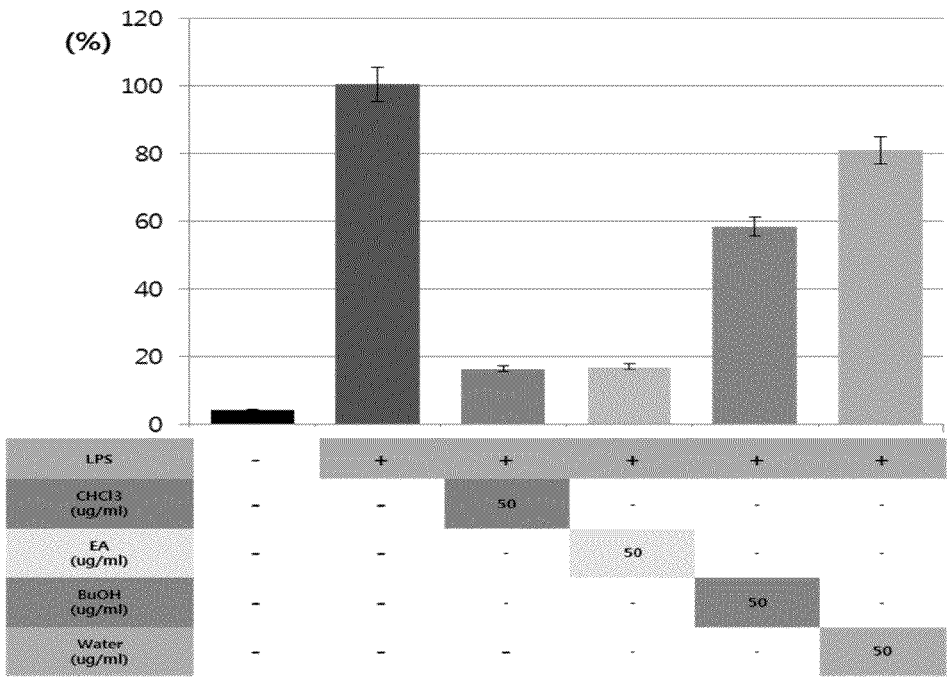
FIG. 11 is a graph showing levels of secreted NO measured to determine anti-inflammatory effects of different solvent fractions of the *Stauntonia Hexaphylla* leaf hot water extract using RAW264.7 cell lines according to an embodiment of the present invention, wherein + means treated with LPS (1 μg/Ml) or the solvent fraction, − means not treated with any sample, characters and values of a horizontal axis represent types and doses (50 μg/Ml) of different solvent fractions of the *Stauntonia Hexaphylla* leaf hot water extract and a vertical axis represents relative NO secretion (%) as compared to a control group treated only with LPS.

In addition, as can be seen from FIG. 11, the water fraction exhibited almost no decrease in NO secretion, when treated with the extract at a concentration of 50 μg/Ml which had been determined to enable all fractions to be safe in Example 2. In addition, the butanol fraction was found to exhibit NO secretion corresponding to 60% of the control group and was thus considered to have anti-inflammatory effect. Meanwhile, the chloroform fraction and the ethyl acetate fraction of the *Stauntonia Hexaphylla* leaf hot water extract exhibited NO secretions which were equal to or less than 20% of the control group. This demonstrated that the ethyl acetate fraction and the chloroform fraction had remarkably excellent inhibitory effect on NO production at a concentration having no effect on cytotoxicity.

Example 4

Determination of Anti-Inflammatory Effect Through Measurement of Inflammation-Associated Cytokine mRNA Levels To ascertain anti-inflammatory effect of the *Stauntonia Hexaphylla* leaf hot water extract which had been determined to exhibit superior anti-inflammatory effect based on NO secretion in Example 3 again, variation in mRNA level of inflammatory response-associated cytokine, specifically, iNOS was ascertained using macrophage primary cells.

In order to obtain macrophage primary cells, 32 4-week old male mice (ICR mouse) having a body weight of 15 g to 20 g and 32 Sprague-Dawley mice were obtained from Samtako Inc. (Korea), the respective mice were classified into 16 groups and 4 mice per group were placed and bred. The test animals were bred at a temperature of 20° C. to 24° C. and at a humidity of 60% to 70% under the day-night illumination condition at 12-hour intervals, and were freely fed with water and feed. The feed used herein was a solid feed (Samyang Feed Co., Korea). The test animals were bred under the same conditions for 7 days, adapted to laboratory environments and used for further testing.

Macrophage primary cells ($2 \times 10^6$ cells/ml) obtained from the test animals were cultured in a serum starvation medium for 24 hours. After culturing, the cells were treated with LPS (0.5 mg/ml) or LPS (0.5 mg/ml) and different concentrations of the *Stauntonia Hexaphylla* leaf hot water extract and cultured for 24 hours. After 24 hours, RNA was isolated from the cultured cells. The RNA isolation was performed by the following method.

Specifically, the cultured cells were lysed in a GIT solution (easy BLUE Total RNA extraction kit, Intron Biotechnology Inc., Korea), and centrifuged at room temperature at 10,000 rpm for 5 minutes, and a supernatant was discarded to obtain a pellet. 1 ml of 0.1% DEPC solution (Sigma, USA) was added to the pellet, the resulting mixture was centrifuged at 12,000 rpm for 2 minutes again, and the supernatant was discarded to obtain a pellet. 0.5 ml of guanidinium was added to the obtained pellet, followed by vortexing. Furthermore, 0.5 ml of a phenol/chloroform/iso-amylalcohol mix solution (25:24:1) was added to the resulting mixture, followed by vortexing and centrifugation at 12,000 rpm for 3 minutes to obtain a supernatant. The supernatant was homogeneously mixed with an equal amount of iso-propylalcohol and allowed to stand at −20° C. for 30 minutes. Then, the resulting mixture was centrifuged at 12,000 rpm for 10 minutes, the supernatant was discarded, and the pellet was washed with a 70% aqueous ethanol solution and was dried under vacuum to isolate RNA.

The isolated RNA was dissolved in 1 ml of a 0.1% DEPC solution and was used to measure a content of mRNA of inflammation-associated cytokine. The mRNA content of the inflammation-associated cytokine, iNOS, was measured in accordance with the following method.

Superscript II reverse transcriptase (Invitrogen, USA) was added to 3 μg of the isolated RNA, followed by incubation at 42° C. for 105 minutes and then at 70° C. for 15 minutes, to obtain cDNA. The obtained cDNA was quantified by real-time PCR. Primer sequences and test conditions used for real-time PCR are shown in the following Table 1.

TABLE 1

| Target mRNA | | Primer sequence | SEQ ID NO | Annealing Tm(° C.) |
|---|---|---|---|---|
| iNOS | Sense | CAGAGGACCCAGAGACAAG | 1 | 50.8 |
| iNOS | Anti-sense | ACCTGATGTTGCCATTGTTG | 2 | |

Figure 6:
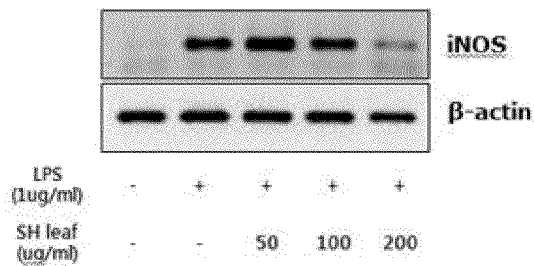
FIG. 6 is a graph showing mRNA levels of inflammation-associated cytokine measured to determine anti-inflammatory effects of the *Stauntonia Hexaphylla* leaf hot water extract according to an embodiment of the present invention, wherein + means treated with LPS (1 μg/Ml) or a solvent fraction, − means non-treated with any sample, and a value of a horizontal axis represents a dose (μg/Ml) of the *Stauntonia Hexaphylla* leaf hot water extract.

As a result of real-time PCR, an image showing comparison of iNOS content with β-actin content is shown in FIG. 6.

As shown in FIG. 6, a control group not treated with LPS did not exhibit mRNA of inflammation-associated cytokine, iNOS, at all, whereas a group treated only with LPS exhibited a remarkably high level of mRNA of iNOS. In addition, a group treated with the *Stauntonia Hexaphylla* leaf hot water extract prepared in Example 1, in spite of being treated with LPS, exhibited a concentration-dependent decrease in mRNA content of iNOS. The concentration-dependent decrease in iNOS mRNA content upon treatment with the *Stauntonia Hexaphylla* leaf hot water extract demonstrated that the *Stauntonia Hexaphylla* leaf hot water extract exhibited superior anti-inflammatory effects.

Example 5

Determination of Inhibitory Activity on Expression of Inflammation-Associated iNOS and COX-2

To ascertain anti-inflammatory effect of the *Stauntonia Hexaphylla* leaf hot water extract which had been determined to exhibit superior anti-inflammatory effect based on NO secretion and decrease in mRNA content of iNOS in Examples 3 and 4 again, inhibitory activity on expression of iNOS and COX-2 was confirmed.

Specifically, the macrophage primary cells obtained in Example 4 were plated on a 24 well plate at a density of $1 \times 10^5$ cells/ml controlled using a DMEM medium and pre-incubated in a 5% $CO_2$ incubator for 18 hours. After pre-culturing, the cells were treated with the *Stauntonia Hexaphylla* leaf hot water extract at different concentrations (0.1 μg/Ml, 1 μg/Ml, 10 μg/Ml, 100 μg/Ml and 200 μg/Ml), cultured for one hour, treated with LPS (1 μg/Ml) and cultured under the same conditions as the pre-culturing. After culturing for 24 hours, the cells were harvested, washed with phosphate buffered saline (PBS) three times, dissolved in cell lysis buffer (50 mM Tris-HCl (pH 7.5), 150 mM NaCl, 1% Nonidet P-40, 2 mM EDTA, 1 mM EGTA, 1 mM NaVO3, 10 mM NaF, 1 mM dithiothreitol, 1 mM phenylmethylsulfonyl fluoride, 25 μg/Ml aprotinin, 25 μg/Ml leupeptin) at 4° C. for 30 minutes, and centrifuged at 4° C. and 15,000 rpm for 15 minutes to remove cell membrane ingredients.

Protein concentration was quantified by standardizing bovine serum albumin (BSA) and using Bio-Rad Protein Assay Kit. 20 μg of the isolated protein was loaded on a 10% mini gel SDS-PAGE, and degenerated and separated, the protein was transferred to a nitrocellulose membrane (BIO-RAD, Richmond, Calif., USA) at 350 mA for one hour. The protein-transferred membrane was blocked in a TTBS (0.1% Tween 20+TBS) solution containing 5% skim milk at room temperature for 2 hours.

An anti-mouse iNOS (Calbiochem, La Jolla, USA) as an antibody used to detect an amount of expressed iNOS, and an anti-mouse COX-2 (BD Biosciences Pharmingen, San Jose, USA) as an antibody used to detect an amount of expressed COX-2, were diluted in TTBS solution at 1:1,000, reacted at room temperature for 2 hours and washed with TTBS three times. HRP (horse radish peroxidase)-conjugated anti-mouse IgG (Amersham Pharmacia Biotech, Little Chalfont, UK) as a secondary antibody was diluted at 1:5,000, reacted at room temperature for 30 minutes, washed with TTBS three times, and reacted with an ECL substrate (Amersham Biosciences, Piscataway, N.J., USA) for 30 seconds and amounts of expressed iNOS and COX-2 were measured using a chemi-luminescence imaging system (ATTO AE-9150 EZ-Capture II, Japan). Measurement results of the expressed amounts are shown in FIG. 7.

Figure 7:
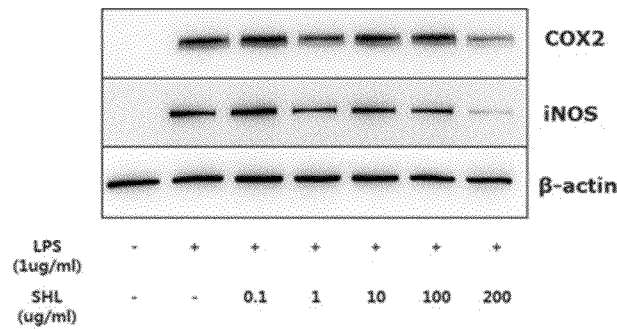
FIG. 7 is a graph showing expression of iNOS and COX-2 measured to determine anti-inflammatory effects of the *Stauntonia Hexaphylla* leaf hot water extract according to an embodiment of the present invention wherein, + means treated with LPS (1 μg/Ml) or a solvent fraction, − means non-treated with any sample, and a value of a horizontal axis represents a dose (μg/Ml) of the *Stauntonia Hexaphylla* leaf hot water extract.

As can be seen from FIG. 7, a control group not treated with LPS did not exhibit inflammation-associated proteins, that is, iNOS and COX-2, whereas a group treated only with LPS exhibited remarkably high levels of iNOS and COX-2. In addition, a group treated with the *Stauntonia Hexaphylla* leaf hot water extract prepared in Example 1, in spite of treatment with LPS, exhibited a concentration-dependent decrease in iNOS and COX-2 contents. The concentration-dependent decrease in iNOS and COX-2 contents upon treatment with the *Stauntonia Hexaphylla* leaf hot water extract demonstrated that the *Stauntonia Hexaphylla* leaf hot water extract exhibited superior anti-inflammatory effects.

Example 6

Determination of Anti-Inflammatory Effect Through Measurement of Inflammation-Associated Cytokine mRNA Levels In order to determine anti-inflammatory effect of the *Stauntonia Hexaphylla* fruit hot water extract prepared in Example 1, variation in mRNA content of inflammatory response-associated cytokine was ascertained using macrophage primary cells.

In order to obtain the macrophage primary cells, 32 4-week male mice (ICR mouse) having a body weight of 15 g to 20 g and 32 Sprague-Dawley mice were obtained from Samtako Inc. (Korea), the respective mice were divided into 16 groups and 4 mice per group were placed and bred. The test animals were bred at a temperature of 20° C. to 24° C. and at a humidity of 60% to 70% under the day-night illumination condition at 12-hour intervals and were freely fed with water and feed. The feed used herein was a solid feed (Samyang Feed Co., Korea). The test animals were bred under the same conditions for 7 days, adapted to laboratory environments and used for further tests.

Macrophage primary cells ($2 \times 10^6$ cells/ml) obtained from the test animals were cultured in a serum starvation medium for 24 hours. After culturing, the cells were treated with LPS (0.5 mg/ml), or LPS (0.5 mg/ml) and different concentrations of the *Stauntonia Hexaphylla* leaf hot water extract and cultured for 24 hours. After 24 hours, RNA was isolated from the cultured cells. The RNA isolation was performed by the following method.

Specifically, the cultured cells were lysed in a GIT solution (easy BLUE Total RNA extraction kit, Intron Biotechnology Inc., Korea), and centrifuged at room temperature at 10,000 rpm for 5 minutes, and a supernatant was discarded to obtain a pellet. 1 ml of 0.1% DEPC solution (Sigma, USA) was added to the pellet, the resulting mixture was centrifuged at 12,000 rpm for 2 minutes again, and the supernatant was discarded to obtain a pellet. 0.5 ml of guanidinium was added to the obtained pellet, followed by vortexing. Furthermore, 0.5 ml of a phenol/chloroform/iso-amylalcohol mix solution (25:24:1) was added to the resulting mixture, followed by vortexing and centrifugation at 12,000 rpm for 3 minutes to obtain a supernatant. The supernatant was homogeneously mixed with an equal amount of iso-propylalcohol and allowed to stand at −20° C. for 30 minutes. Then, the resulting mixture was centrifuged at 12,000 rpm for 10 minutes, the supernatant was discarded, and the pellet was washed with a 70% aqueous ethanol solution and was dried under vacuum to isolate RNA.

The isolated RNA was dissolved in 1 ml of a 0.1% DEPC solution and was then used to measure a content of mRNA of inflammation-associated cytokine. The mRNA contents of the inflammation-associated cytokines, IL-1β, IFN-γ and TNF-a, were measured by the following method.

Superscript II reverse transcriptase (Invitrogen, USA) was added to 3 μg of the isolated RNA, followed by incubation at 42° C. for 105 minutes and then at 70° C. for 15 minutes, to obtain cDNA. The obtained cDNA was quantified by real-time PCR. Primer sequences and test conditions used for the real-time PCR are shown in the following Table 2.

TABLE 2

| Target mRNA | | Primer sequence | SEQ ID NO | Annealing Tm (° C.) |
|---|---|---|---|---|
| TNF-a | Sense | GGCAGGTCTACTTTGGAGTCATTGC | 3 | 62.2 |
| | Anti-sense | ACATTCGAGGCTCCAGTGAATTCGG | 4 | |
| IFN-γ | Sense | GCGGCTGACTGAACTCAGATTGTAG | 5 | 50 |
| | Anti-sense | GTCACAGTTTTCAGCTGTATAGGG | 6 | |
| IL-1β | Sense | TGCAGAGTTCCTACATGGTCAACC | 7 | 55 |
| | Anti-sense | GTGCTGCCTAATGTCCCCTTGAATC | 8 | |

Figure 8:
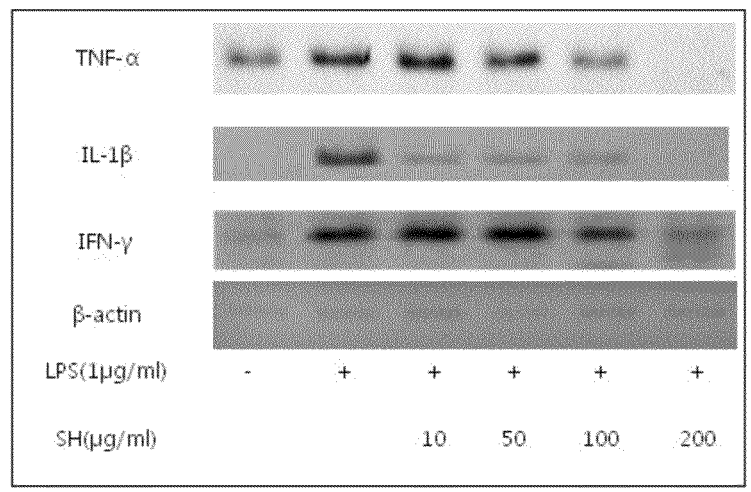
FIG. 8 is a graph showing levels of transferred mRNA of inflammation-associated cytokines detected by RT-PCR to determine anti-inflammatory effects of the *Stauntonia Hexaphylla* fruit hot water extract according to an embodiment of the present invention using macrophage primary cells, wherein + means treated with LPS (1 μg/Ml), − means non-treated with LPS (1 μg/Ml), an SHL value of a horizontal axis represents a dose (μg/Ml) of the *Stauntonia Hexaphylla* fruit hot water extract and a vertical axis represents a type of cytokines.

As a result of real-time PCR, an image showing comparison of IL-1β, IFN-γ and TNF-a contents with β-actin content is shown in FIG. 8.

As shown in FIG. 8, a control group not treated with LPS did not exhibit mRNAs of inflammation-associated cytokines, IL-1β, IFN-γ and TNF-a, at all, whereas a group treated only with LPS exhibited remarkably high levels of mRNAs of IL-1β, IFN-γ and TNF-a IL-1β. In addition, a group treated with the *Stauntonia Hexaphylla* fruit hot water extract prepared in Example 1, in spite of treatment with LPS exhibited a concentration-dependent decrease in mRNA contents of IL-1β, IFN-γ and TNF-a, in particular, a prominent decrease in mRNA content of IL-1β.

Example 7

Determination of Anti-Inflammatory Effect Through Measurement of Inflammation-Associated Cytokine, TNF-a, Level To ascertain anti-inflammatory effects of the *Stauntonia Hexaphylla* fruit hot water extract which had been determined to exhibit superior anti-inflammatory effect based on variation in mRNA content of inflammatory response-associated cytokine in Example 6, again, variation in TNF-a among inflammatory response-associated cytokine was confirmed using macrophage primary cells.

The macrophage primary cells were obtained by breeding test animals in the same manner as in Example 6. Macrophage primary cells ($2 \times 10^6$ cells/ml) obtained from the test animals were cultured in the same manner as in Example 5. Measurement of amount of produced TNF-a was carried out using an image analysis program (UVIband) supplied from UVITEC fluorescence imaging systems.

Specifically, TNF-a and β-actin bands separated by agarose gel electrophoresis were image-scanned through the UVITEC fluorescence imaging system. Volumes (intensities) of TNF-a bands and β-actin bands of a normal group, a control group induced by LPS, and experimental groups treated with different concentrations of the *Stauntonia Hexaphylla* fruit extract were quantified from the scanned images using an image analysis program (UVIband). TNF-a content was determined as a relative content of TNF-a with respect to β-actin expressed in the normal group (relative %, TNF-a/β-actin) and results were shown in FIG. 9.

Figure 9:
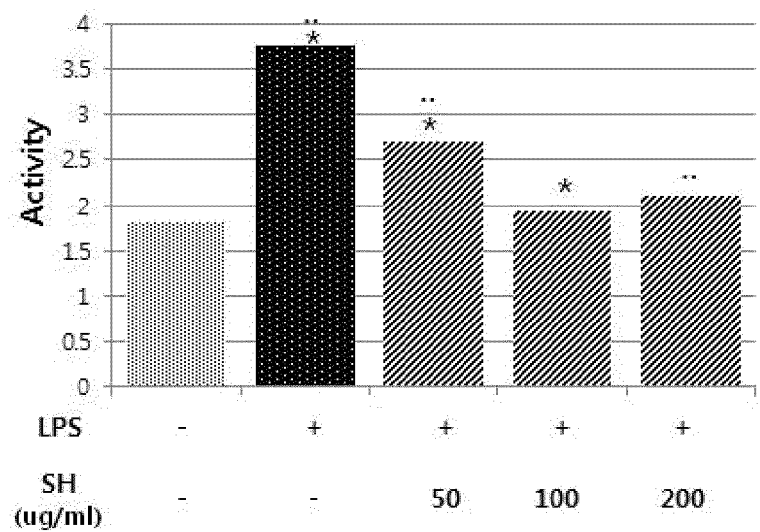
FIG. 9 is a graph showing produced levels of TNF-α among inflammation-associated cytokines to determine anti-inflammatory effects of the *Stauntonia Hexaphylla* fruit hot water extract using macrophage primary cells according to an embodiment of the present invention, wherein + means treated together with LPS (1 μg/Ml), − means non-treated with LPS, a horizontal axis represents a dose (μg/Ml) of the *Stauntonia Hexaphylla* fruit hot water extract and a vertical axis represents a level of produced TNF-α.

As can be seen from FIG. 9, a control group not treated with LPS was determined to exhibit a small level of inflammation-associated cytokin, that is, TNF-a, whereas a group treated only with LPS exhibited a remarkably high level of TNF-a. In addition, a group treated with the *Stauntonia Hexaphylla* fruit hot water extract prepared in Example 1, in spite of treatment with LPS was determined to exhibit a concentration-dependent decrease in TNF-a content.

Example 8

Determination of Inhibitory Effect of Fraction Against COX-2 (cyclooxygenase-2)

To ascertain anti-inflammatory effect of the fraction of the *Stauntonia Hexaphylla* leaf hot water extract which had been determined to exhibit superior anti-inflammatory effect based on NO secretion in Example 3 again, inhibitory activity against COX-2 enzyme was confirmed.

First, 5-week old Sprague-Dawley male white mice (Samtako Inc. Korea) were adapted to laboratory environments for 7 days and used for testing. The test animals were bred at a temperature of 20° C. to 24° C., at a humidity of 60% to 70% under the day-night illumination condition at 12-hour intervals and were freely fed with water and feed. The feed used herein was a solid feed (Samyang Feed Co., Korea). The test animals were bred under the same conditions for 7 days, adapted to laboratory environments and then used for testing.

The abdomen of the test animals (SD male white mice) was administered with 10 ml of 4% thioglycolate, and abdominal macrophage primary cells were proliferated for 3 days and the mice were cervically dislocated. Abdominal macrophage primary cells were collected from the SD male white mice prepared by cervical dislocation.

Specifically, after 10 ml of HBSS was added to the abdomen, abdominal macrophage primary cells were collected using a syringe and transferred to a conical tube. The abdominal macrophage primary cells were centrifuged at 13,000 rpm for 5 minutes, washed with a DMEM medium twice, seeded on a petri dish having a diameter of 60 mm and incubated in a $CO_2$ cell incubator for 4 hours. After incubation, floating cells were removed and adhered cells were stabilized for 24 hours, then proteins were isolated from the cells, which were further used.

The isolated proteins were treated with 50 mg/ml of the fractions of the *Stauntonia Hexaphylla* leaf hot water extract obtained in Example 1, stabilized for 30 minutes and cyclooxygenase enzyme activity was measured using a COX fluorescent activity assay kit (Cayman Chemical Company, Item No. 700200). Results of the measured enzyme activity are shown in FIG. 12.

Figure 12:
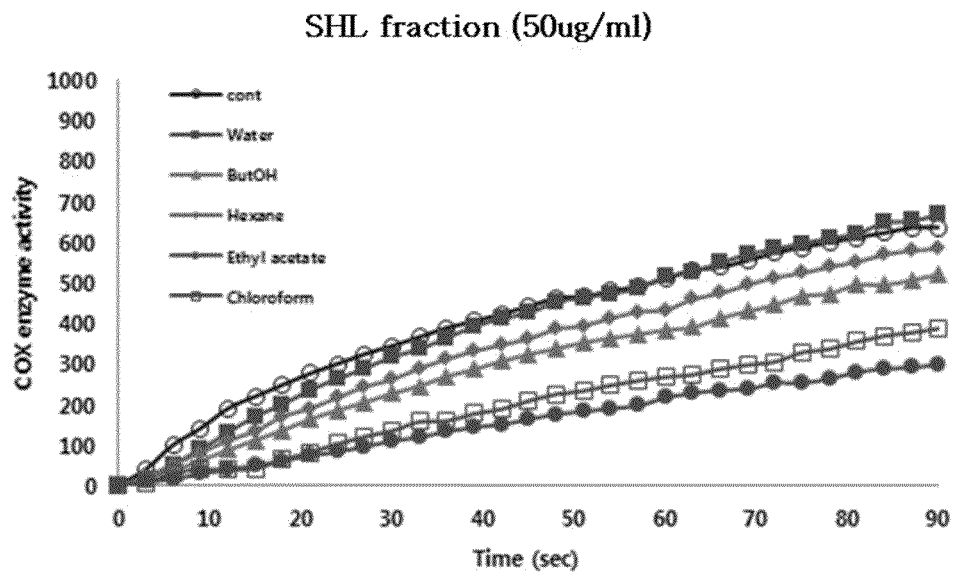
FIG. 12 is a graph showing COX-2 inhibitory activity measured based on COX-2 activity to determine anti-inflammatory effects of the solvent fractions of the *Stauntonia Hexaphylla* leaf hot water extract according to an embodiment of the present invention, wherein solvents distinguishing different curves represent fractionation solvents, a horizontal axis represents time passed after treatment and a vertical axis represents COX-2 activity.

As can be seen from FIG. 12, the water fraction of the *Stauntonia Hexaphylla* leaf hot water extract did not exhibit any inhibitory effects, and the hexane fraction and the butanol fraction exhibited low inhibitory activity, whereas the ethyl acetate fraction and the chloroform fraction exhibited remarkably superior inhibitory activity. In particular, difference in inhibitory activity was prominent with the passage of time. In particular, the ethyl acetate fraction of the *Stauntonia Hexaphylla* leaf hot water extract exhibited the most superior COX-2 inhibitory activity.

Example 9

Determination of Antipyretic Effects of Extracts and Fractions 9-1. Determination of Antipyretic Effect of *Stauntonia Hexaphylla* Leaf Extract Test animals were used to determine antipyretic effects of the *Stauntonia Hexaphylla* leaf extract and fractions thereof prepared in Example 1.

The test animals herein used were 5-week old Sprague-Dawley male white mice obtained from Samtako Inc. (Korea). The test animals were bred at a temperature of 20° C. to 24° C. and at a humidity of 60% to 70% under the day-night illumination condition at 12-hour intervals and were freely fed with water and feed. The feed used herein was a solid feed (Samyang Feed Co., Korea). The test animals were bred under the same conditions for 7 days, adapted to laboratory environments and then used for testing.

The test of fever induced by lipopolysaccharide (LPS) as a bacterial endotoxin to ascertain antipyretic efficacy using the test animals was carried out using a method suggested by Vilela F C et. al (Anti-inflammatory and antipyretic effects of *Sonchus oleraceus* in rats. J Ethnopharmacol. 17; 127(3): 737-41 (2010)).

Specifically, 5 mice were randomly selected from the test animals and set as a first group, and 500 μg/kg of lipopolysaccharide (LPS, Sigma, USA) was intraperitoneally injected into the mice to induce fever. Body temperature was measured as follows. Rectal body temperature was measured using a rectal thermometer (Portable Thermocouple Thermometer (Physitemp Instruments, USA) and a stainless steel rectal probe for rats (Physitemp Instruments, USA) and body temperatures of SD mice were measured three times before the test to minimize an temperature increase caused by temperature measurement stress.

First, in order to determine antipyretic effects of the *Stauntonia Hexaphylla* leaf hot water extract, a negative control group (LPS) not treated with any sample, a first positive control group (APAP) orally administered with 50 mg/kg of acetaminophen (APAP, Sigma, USA), a conventional drug, found to have antipyretic effect, and a second positive control group (Dexamethasone) orally administered with 1 mg/kg of dexamethasone (Sigma, USA) were used.

First, 500 μg/kg of a fever-inducing substance (LPS) was intraperitoneally injected (i.p.) into the test animals that finished preparations for minimization of temperature increase caused by temperature measurement stress, and a non-treated group (LPS), a group (SHL-200) orally administered with 200 mg/kg of the *Stauntonia Hexaphylla* leaf hot water extraction, a group (APAP) orally administered with 50 mg/kg of acetaminophen, and a group (Dexamethasone) orally administered with 1 mg/kg of dexamethasone were prepared according to type of test groups. In addition, 200 mg/kg of the *Stauntonia Hexaphylla* leaf hot water extract was orally administered one hour after administration of the fever-inducing substance (SHL-200 (1 h)), and rectal temperatures were measured at one hour, 4 hours and 8 hours over 8 hours in total after the administration of the fever-inducing substance. The measurement results are shown in FIG. 12 and the following Table 3. Values of the following Table 3 mean body temperatures (° C.) measured at different times.

9-2. Determination of Antipyretic Effect of Fraction of *Stauntonia Hexaphylla* Leaf Extract In order to determine antipyretic effects of the fraction of the *Stauntonia Hexaphylla* leaf extract prepared in Example 1-2, test animals (5-week old SD male white mice (Samtako Inc., Korea)) bred in the same manner as in Example 9-1 were used.

Like Example 9-1 to determine antipyretic efficacy using the test animals, LPS-induced fever was carried out using a bacterial endotoxin (Lipopolysaccharide (LPS) from *E. coli* 0111:B4 (Sigma, USA)) by a method suggested by Vilela F C et. al., and body temperature was measured using a rectal thermometer.

First, in order to determine antipyretic effects of the *Stauntonia Hexaphylla* leaf hot water extract, a negative control group (LPS) not administered with any sample, and a positive control group (Ibuprofen) orally administered with ibuprofen (Daewoong Pharmaceutical Co., Ltd., Korea) as a conventional drug known to have antipyretic effect were used. In addition, a hexane fraction (Hx), a chloroform fraction ($CHCl_3$), an ethyl acetate fraction (EA) and a butanol fraction (BuOH) were respectively administered in a dose of 20 mg/kg to experimental groups.

First, rectal body temperatures of test animals were measured three times using a body thermometer (Portable Thermocouple Thermometer, physitemp, USA) before the test to minimize temperature increase caused by temperature measurement stress.

TABLE 3

|     | Normal          | LPS             | SHL 200         | SHL 200 (1 h)   | Dexamethasone   | APAP            |
| --- | --------------- | --------------- | --------------- | --------------- | --------------- | --------------- |
| 0 h | 37.2            | 37.2            | 37.2            | 37.2            | 37.2            | 37.2            |
| 1 h | 37.55 ± 0.21    | 38.2 ± 0.68     | 36.65 ± 0.69    | 38.23 ± 0.41    | 37.3 ± 0.52     | 36.58 ± 0.67    |
| 4 h | 37.65 ± 0.07    | 37.85 ± 0.33    | 37.20 ± 0.45    | 36.95 ± 0.54    | 37.6 ± 0.12     | 37.53 ± 0.59    |
| 8 h | 37.55 ± 0.07    | 37.6 ± 0.61     | 37.7 ± 0.14     | 37.73 ± 0.22    | 37.73 ± 0.13    | 37.78 ± 0.13    |

Figure 13:
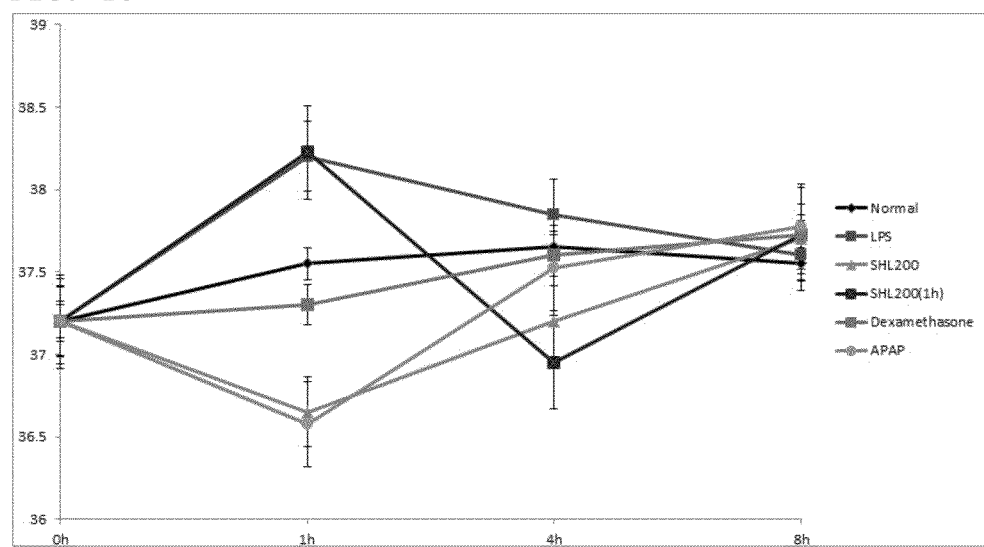
FIG. 13 is a graph showing results of alleviation of fever induced by LPS in order to determine anti-inflammatory effects of the *Stauntonia Hexaphylla* leaf hot water extract using test animals according to an embodiment of the present invention, wherein a value of a horizontal axis represents time (hour, h) passed after administration with samples and a value of a vertical axis represents a measured body temperature.

As can be seen from FIG. 13 and Table 3, the group administered with the fever-inducing substance (LPS) exhibited a sharp increase by about 1° C. to 1.8° C. or more, from one hour onwards. However, the group administered with the *Stauntonia Hexaphylla* leaf hot water extract (SHL-200) according to the present invention exhibited a remarkable decrease in body temperature. This decrease was greater than that of the group (Dexamethasone) orally administered with 1 mg/kg of dexamethasone and was substantially equivalent to that of the group (APAP) orally administered with 50 mg/kg of acetaminophen generally used as an antipyretic drug, which demonstrated that SHL-200 exhibited the superior antipyretic effects. On 4 hours after administration, SHL-200 did not exhibited an increase in body temperature, as compared to the group (APAP) orally administered with 50 mg/kg of acetaminophen, which demonstrated that SHL-200 also exhibited superior persistence.

In addition, in case of a group (SHL-200(1 h)) orally administered with 200 mg/kg of the *Stauntonia Hexaphylla* leaf hot water extract at one hour after administration of the fever-inducing substance (LPS), body temperature was sharply increased like the control group and then was considerably decreased and on 4 hours, decreased to a level, similar to the group (APAP) orally administered with the fever-inducing substance and 50 mg/kg of acetaminophen, which demonstrated the *Stauntonia Hexaphylla* leaf hot water extract exerted effective actions even after fever began, that is, body temperature was elevated to a predetermined level.

The test animals subjected to temperature measurement were orally administered with different contents of respective samples at 5 minutes before administration of the fever-inducing substance, the bacterial endotoxin (LPS), after 5 minutes, 500 μg/kg of the bacterial endotoxin was intraperitoneally injected (i.p.) into the animals, and rectal body temperature of test animals was measured at intervals of 30 minutes for 2 hours. Measurement results are shown in FIG. 14.

Figure 14:
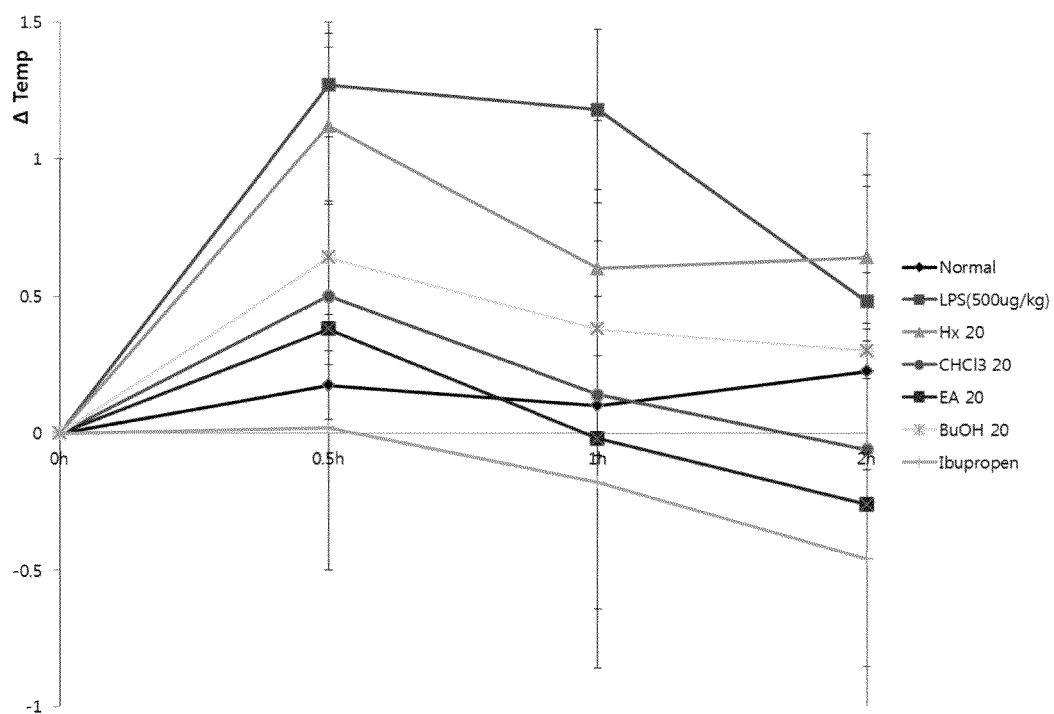
FIG. 14 is a graph showing results of alleviation of fever induced by LPS in order to determine anti-inflammatory effects of the fractions of the *Stauntonia Hexaphylla* leaf hot water extract according to an embodiment of the present invention using test animals, wherein a value of a horizontal axis represent time (hour, h) passed after administration with samples and values of a vertical axis represent variation in body temperature changed from a body temperature measured before sample administration, that is, value calculated by subtracting a body temperature of a test animal measured before sample administration from a body temperature of the test animal measured at the corresponding time.

As can be seen from FIG. 14, the normal group (Normal) not administered with any sample exhibited almost no variation in body temperature, but the group administered with the fever-inducing substance (LPS) exhibited a sharp increase in body temperature by 1° C. or higher from 30 minutes onward after the administration, maintained the body temperature increased by about 1° C. even at one hour, and exhibited an increase in body temperature by about 0.5° C. even at 2 hours. Meanwhile, when the group administered with the hexane fraction of the *Stauntonia Hexaphylla* leaf hot water extract was small temperature increment, but exhibited a rather high final temperature at 2 hours, as compared to the group administered with the fever-inducing substance. The butanol fraction exhibited a small temperature increment and an overall low body temperature increase effect, as compared to the hexane fraction. Meanwhile, the group administered with the chloroform fraction exhibited an increase in body temperature in an early stage, but returned to a substantially normal body temperature at 2 hours, which demonstrated that the group administered with the chloroform fraction exhibited inhibitory effect on increase in body temperature, that is, antipyretic effect. The body temperature of the ethyl acetate fraction returned to a normal body temperature at 1 hour, but was lower than an initial temperature at 2 hours. This demonstrated that the ethyl acetate fraction exhibited remarkably superior antipyretic effect comparable to ibuprofen generally used as an antipyretic drug and demonstrated to have antipyretic effects.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An anti-inflammatory composition, comprising:
    a *Stauntonia Hexaphylla* fraction as an active ingredient that is made by extracting *Stauntonia Hexaphylla* leaf by boiling in water at 100° C. for 3 hours, separating into hexane soluble and insoluble layer, and using chloroform or ethyl acetate to fractionate the hexane insoluble layer; and
    a pharmaceutically acceptable carrier.

2. A cosmetic composition for relieving or alleviating inflammation, comprising:
    a *Stauntonia Hexaphylla* fraction as an active ingredient that is made by extracting *Stauntonia Hexaphylla* leaf by boiling in water at 100° C. for 3 hours, separating into hexane soluble and insoluble layer, and using chloroform or ethyl acetate to fractionate the hexane insoluble layer; and
    a pharmaceutically acceptable carrier.

3. An antipyretic composition, comprising:
    a *Stauntonia Hexaphylla* fraction as an active ingredient that is made by extracting *Stauntonia Hexaphylla* leaf by boiling in water at 100° C. for 3 hours, separating into hexane soluble and insoluble layer, and using chloroform or ethyl acetate to fractionate the hexane insoluble layer; and
    a pharmaceutically acceptable carrier.

4. The antipyretic composition according to claim 3, wherein the fractionation solvent is ethyl acetate.

5. The antipyretic composition according to claim 3, wherein the antipyretic composition is an antipyretic drug, or an antipyretic and analgesic drug.

* * * * *